(12) United States Patent
Holmquist et al.

(10) Patent No.: US 11,536,733 B2
(45) Date of Patent: Dec. 27, 2022

(54) METHODS AND SYSTEMS FOR THE DETECTION OF 11-OXO ANDROGENS BY LC-MS/MS

(71) Applicant: Laboratory Corporation of America Holdings, Burlington, NC (US)

(72) Inventors: Brett Holmquist, Thousand Oaks, CA (US); Donald Walt Chandler, Agoura Hills, CA (US); Russell Philip Grant, Chapel Hill, NC (US); William Curtin, Northridge, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 179 days.

(21) Appl. No.: 16/850,786

(22) Filed: Apr. 16, 2020

(65) Prior Publication Data
US 2020/0333361 A1    Oct. 22, 2020

Related U.S. Application Data

(60) Provisional application No. 62/834,738, filed on Apr. 16, 2019.

(51) Int. Cl.
*G01N 33/74* (2006.01)
*G01N 30/04* (2006.01)
(Continued)

(52) U.S. Cl.
CPC .......... *G01N 33/743* (2013.01); *G01N 30/04* (2013.01); *G01N 30/7233* (2013.01); *G01N 2030/027* (2013.01); *G01N 2030/045* (2013.01); *G01N 2333/575* (2013.01); *G01N 2800/04* (2013.01); *G01N 2800/52* (2013.01)

(58) Field of Classification Search
CPC .. G01N 33/743; G01N 30/04; G01N 30/7233; G01N 2030/027; G01N 2030/045; G01N 2333/575; G01N 2800/04; G01N 2800/52; G01N 2560/00
See application file for complete search history.

(56) References Cited

U.S. PATENT DOCUMENTS 5,772,874 A    6/1998    Quinn et al.
5,795,469 A    8/1998    Quinn et al.
(Continued)

OTHER PUBLICATIONS

Bloem, L. et al., "11β-Hydroxyandrostenedione Returns to the Steroid Arena: Biosynthesis, Metabolism and Function," Molecules 18:13228-13244 (2013).
(Continued)

*Primary Examiner* — David A Vanore
(74) *Attorney, Agent, or Firm* — Kilpatrick Townsend & Stockton LLP

(57) ABSTRACT

Disclosed are methods, systems, and computer program products for using liquid chromatography/tandem mass spectrometry (LC-MS/MS) for the analysis of endogenous biomarkers, such as 11-oxo androgens, in a sample. The 11-oxo androgens may comprise at least one of 11-hydroxy-androstendione (11OHA), 11-hydroxytestosterone (11OHT) or 11-ketotestosterone (11KT). More specifically, the methods, systems, and computer program products are described for detecting and quantifying the amount of an 11-oxo-androgen in a sample.

18 Claims, 5 Drawing Sheets

(51) Int. Cl.
  *G01N 30/72* (2006.01)
  *G01N 30/02* (2006.01)

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 2006/0228808 | A1* | 10/2006 | Clarke ............... G01N 30/7233 436/173 |
| 2008/0128606 | A1* | 6/2008 | Grant .................... G01N 33/78 250/288 |
| 2009/0134325 | A1* | 5/2009 | Goldman ........... G01N 33/6851 250/283 |
| 2010/0059671 | A1* | 3/2010 | Ghoshal ............. G01N 33/6848 250/282 |
| 2010/0084546 | A1* | 4/2010 | Ghoshal ............... G01N 33/743 250/282 |
| 2010/0155594 | A1* | 6/2010 | Goldman ............. G01N 30/724 250/282 |
| 2011/0306080 | A1* | 12/2011 | Chan ................. G01N 33/9473 250/288 |
| 2015/0212055 | A1* | 7/2015 | Yue ...................... H01J 49/004 250/282 |
| 2016/0349221 | A1* | 12/2016 | Goldman ............... G01N 33/49 |
| 2020/0333361 | A1* | 10/2020 | Holmquist ......... G01N 30/7233 |

OTHER PUBLICATIONS

Turcu, A. et al., "11-Oxygenated Androgens are Biomarkers of Adrenal Volume and Testicular Adrenal Rest Tumors in 21-Hydroxylase Deficiency," J. Clin. Endocrinol. Metab. 102(8):2701-2710 (2017).
Pretorius, E. et al., "11-Ketotestosterone and 11-Ketodihydrotestosterone in Castration Resistant Prostate Cancer: Potent Androgens Which Can No Longer Be Ignored," PLoS One 11(7):e0159867 (2016) 17 pages.
Quanson, J.L. et al., "High-throughput analysis of 19 endogenous androgenic steroids by ultra-performance convergence chromatography tandem mass spectrometry," J. Chromatog. B Analyt. Technol. Biomed. Life Sci. 1031:131-138 (2016).
O'Reilly, M. et al., "11-Oxygenated C19 Steroids are the Predominant Androgens in Polycystic Ovary Syndrome," J. Clin. Endocrinol. Metab. 102:840-848 (2017).
Robb, D.B. et al., "Atmospheric pressure photoionization: an ionization method for liquid chromatography-mass spectrometry," Anal. Chem. 72(15): 3653-3659 (2000).
Turcu. A. et al., "Profiles of 21-Carbon Steroids in 21-hydroxylase Deficiency," J. Clin. Endocrinol. Metab., 100:2283-2290 (2015).
Turcu, A. et al., "Adrenal-derived 11-Oxygenated 19-Carbon Steroids are the Dominant Androgens in Classic 21-Hydroxylase Deficiency," Eur. J. Endocrinol, 174(5): 601-609 (2016).
Zimmer, D. et al., "Comparison of turbulent-flow chromatography with automated solid-phase extraction in 96-well plates and liquid-liquid extraction used as plasma sample preparation techniques for liquid chromatography-tandem mass spectrometry," J. Chromatogr. A 854:23-35 (1999).
"Supplementary Table 2. Steroids Measured by LC-MS/MS", (2021) 1 page.
Toit, T. et al., "Profiling Adrenal 11β-Hydroxyandrostenedione Metabolites In Prostate Cancer Cells, Tissue And Plasma:UPC$^2$-MS/MS Quantification Of 11β-hydroxytestosterone, 11Keto-Testosterone And 11Keto-Dihydrotestosterone," The Journal of Steroid Biochemistry and Molecular Biology, 166:54-67 (2017).
Weisser, J. et al., "Two Simple Cleanup Methods Combined With LC-MS/MS For Quantification Of Steroid Hormones In In Vivo And In Vitro Assays," Anal. Bioanal. Chem., 408(18):4883-4895 (2016).
PCT/US2020/028513, International Preliminary Report on Patentability, dated Oct. 28, 2021, 10 pages.
PCT/US2020/028513, International Search Report and Written Opinion, dated Sep. 18, 2020, 14 pages.

\* cited by examiner

METHODS AND SYSTEMS FOR THE DETECTION OF 11-OXO ANDROGENS BY LC-MS/MS

RELATED APPLICATIONS

This application claims priority to U.S. Provisional Patent Application No. 62/834,738, entitled Methods and Systems for the Detection of 11-OXO-Andrgens by LC-MS/MS, filed Apr. 16, 2019. The disclosure of U.S. Provisional Patent Application No. 62/834,738 is incorporated by reference in its entirety herein.

FIELD OF INVENTION

The presently disclosed subject matter relates to methods and systems for the analysis of 11-oxo androgens. In certain embodiments, the 11-oxo androgens are endogenous to human subjects such that the measurement may be used for clinical diagnosis.

BACKGROUND 11-oxygenated (11-oxo) androgens are emerging biomarkers for androgen production of adrenal origin. 11-oxo-androgens include 11-Hydroxy $\Delta_4$androstenedione (11OHA), 11-Ketotestosterone (11KT), and 11-Hydroxytestosterone (11OHT). 11-oxo androgens may play a role in various conditions related to excess androgen levels (Bloem et al., Molecules, 2013, 18, 13228-13244). For example, 11-oxo androgens may be associated with polycystic ovary syndrome (PCOS) (O'Reilly et al., 2017, J. Clin. Endocrinol. Metab., 102:840-848), 21-hydroxylase deficiency (Turcu et al., 2017, J. Clin. Endocrinol. Metab.) and castration resistant prostate cancer (CRPC) (Pretorius et al., Jul. 21, 2016, PLOS ONE).

Although the presence of androgens with oxygen at the 11 position of the steroid backbone have been known for some time, the clinical utility and prevalence of these androgens have only recently come to light. For example, 11KT has been shown to be present in excess levels in PCOS patients and appears to be a better biomarker than testosterone or $\Delta_4$androstenedione for PCOS. The enzyme defect (21-hydroxylase deficiency) that causes congenital adrenal hyperplasia (CAH) also causes excess adrenal androgen production driven by overproduction of adrenocorticotropic hormone (ACTH). The major active adrenal derived androgens are 11-oxo androgens. Eliminating adrenal androgens has been helpful in the treatment of excess androgen-associated conditions, including CRPC. Therefore, 11-oxo androgens may be important to monitor in control of CAH, especially in children and women.

Methods for measurement of androgenic steroids by ultra-performance convergence chromatography tandem mass spectrometry (UPC$^2$-MS/MS) have previously been described (Quanson et al., 2016, J. Chromatog. B, 1031: 131-138; O'Reilly et al., 2017, J. Clin. Endocrinol. Metab., 102:840-848; Pretorius et al., Jul. 21, 2016, PLOS ONE) and LC-MS/MS (Turcu et al., 2017, J. Clin. Endocrinol. Metab., available on-line May 1, 2017; Turcu et al., 2015, J. Clin. Endocrinol. Metab., 100:2283-2290; Turcu et al., 2016, Eur. J. Endocrinol, 174: 601-609).

However, there is a need for a commercially useful assay to provide an accurate measurement of 11-oxo androgens for clinical diagnosis and/or prognosis.

SUMMARY

In certain embodiments, disclosed is a method for determining the presence or amount of at least one biomarker of interest in a sample, the method comprising: providing a sample believed to contain at least one biomarker of interest; chromatographically separating the at least one biomarker of interest from other components in the sample; and analyzing the chromatographically separated at least one biomarker of interest by mass spectrometry to determine the presence or amount of the at least one biomarker of interest in the sample.

In some embodiments, the biomarker of interest is an 11-oxo androgen. In some embodiments, the presently disclosed subject matter provides methods and systems for the quantitative analysis of certain 11-oxo androgens. In certain embodiments, the 11-oxo androgen may comprise at least one of 11-hydroxyandrostendione (11OHA), 11-hydroxytestosterone (11OHT) or 11-ketotestosterone (11KT). In an embodiment, the methods and systems of the present invention allow for measurement of such hormones without the need for derivatization processes.

For example, in one embodiment, disclosed is a method for determining the presence or amount of at least one 11-oxo androgen in a sample by tandem mass spectrometry. The method may comprise any one of the steps of: (a) obtaining a sample from a subject; (b) optionally adding a stable isotope labeled 11-oxo androgen to the sample as an internal standard; (c) performing HPLC; and (d) measuring the 11-oxo androgen (both labeled and unlabeled) by tandem mass spectrometry. In an embodiment, the tandem mass spectrometry may comprise the steps of: (i) generating a precursor ion of the 11-oxo androgen; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the 11-oxo androgen in the sample. In an embodiment, the tandem mass spectrometry is coupled to HPLC. The HPLC step may directly precede the tandem mass spectrometry analysis (i.e., LC-MS/MS). In some embodiments, the HPLC is high turbulence liquid chromatography (HTLC). In some embodiments, the method does not comprise convergence chromatography. In some embodiments, a liquid-liquid extraction is used to partially purify the 11-oxo-androgen prior to HPLC. In some embodiments, duplicate sets of charcoal stripped calibrators are analyzed in each batch.

Another aspect of the disclosure is a system for performing the methods. In some embodiments, the system comprises: a station for providing a test sample suspected of containing one or more 11-oxo androgens; a station for partially purifying the one or more 11-oxo androgens from other components in the sample; a station for chromatographically separating one or more 11-oxo androgen from other components in the sample; and a station for analyzing the chromatographically separated one or more 11-oxo androgens by mass spectrometry to determine the presence or amount of the one or more 11-oxo androgens in the test sample.

An additional aspect of the disclosure is a computer program product tangibly embodied in a non-transitory machine-readable storage medium, including instructions configured to cause one or more data processors to perform actions to measure the presence or amount of at least one 11-oxo androgen in a sample comprising at least one of the following steps: (a) obtaining a sample from a subject; (b) optionally adding a stable isotope-labeled 11-oxo androgen to the sample as an internal standard; (c) performing liquid-liquid extraction; and (d) measuring the 11-oxo androgen by tandem mass spectrometry.

Certain objects of the disclosure, having been stated hereinabove, will become further evident as the description proceeds when taken in connection with the accompanying figures and examples as described herein below.

BRIEF DESCRIPTION OF THE DRAWINGS

Having thus described the invention in general terms, reference will now be made to the non-limiting accompanying drawings, which are not necessarily drawn to scale.

Figure 1:
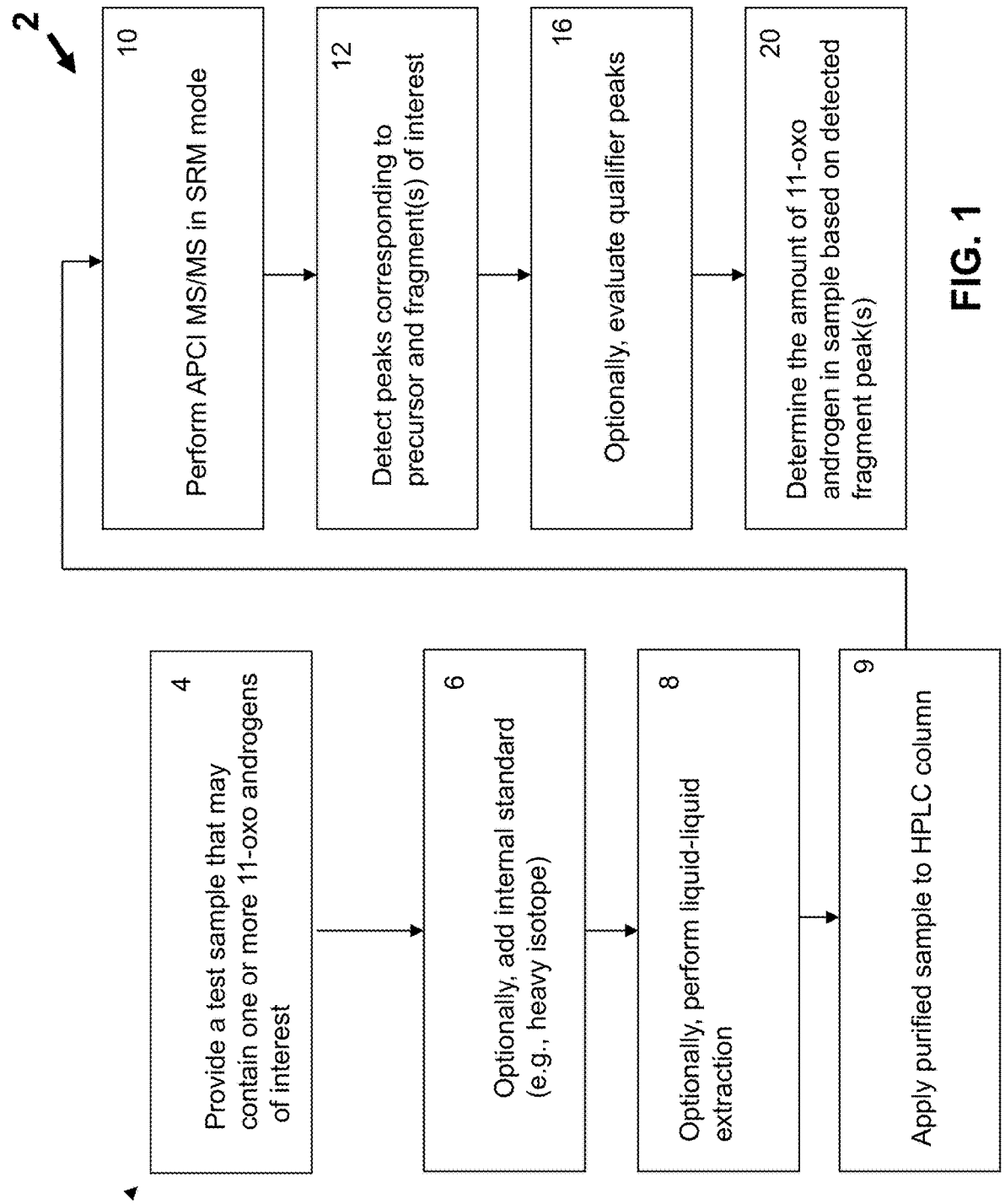

FIG. 1 shows a flow chart of a method for quantitative analysis of an 11-oxo androgen in accordance with one embodiment of the present disclosure.

Figure 2:
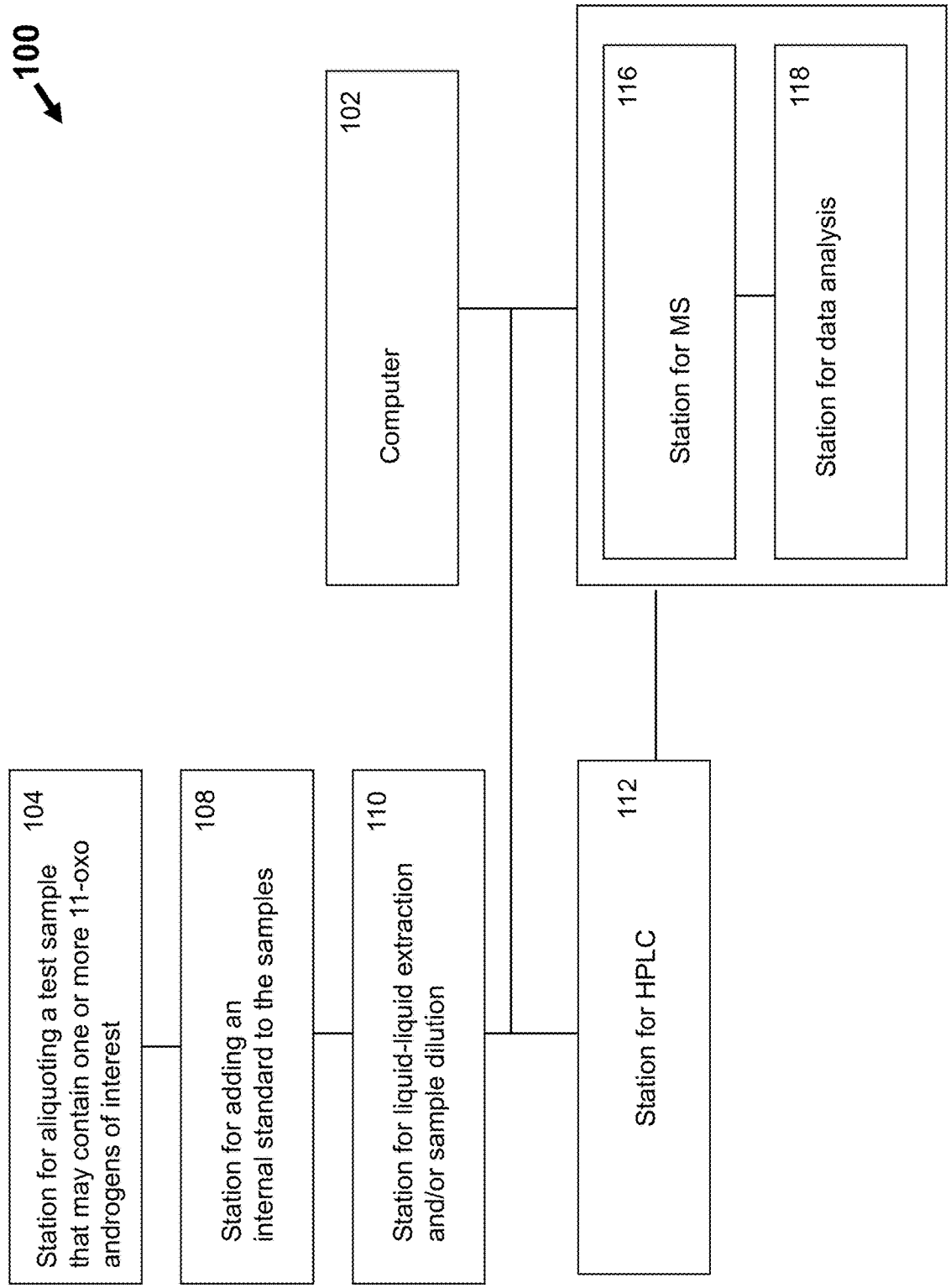

FIG. 2 shows a system for quantitative analysis of an 11-oxo androgen in accordance with one embodiment of the present disclosure.

Figure 3:
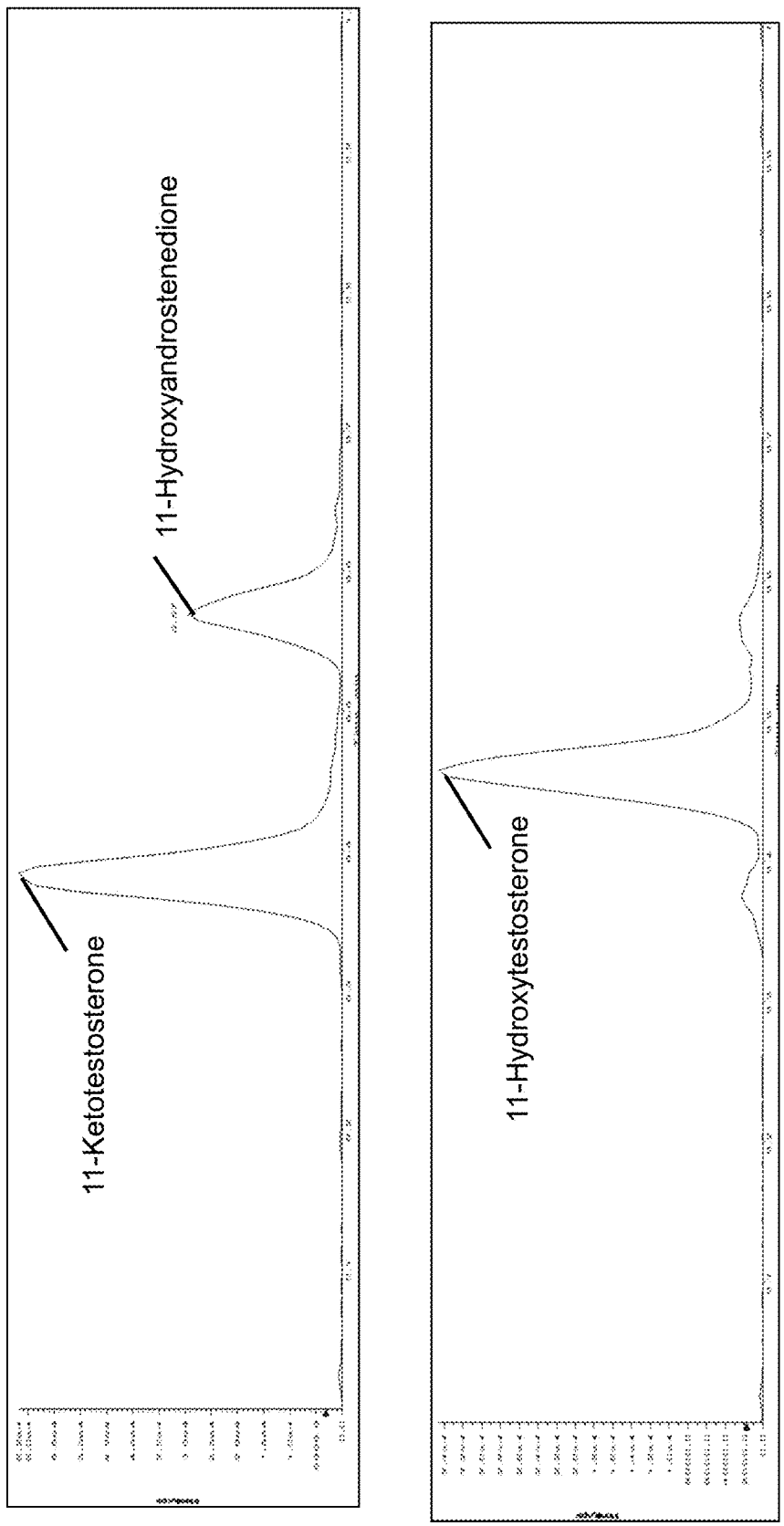

FIG. 3 shows mass chromatograms for 11-ketotestosterone, 11-hydroxy-$\Delta_4$androstenedione and 11-hydroxytestosterone each at 20 ng/dL androgen in accordance with one embodiment of the present disclosure.

Figure 4:
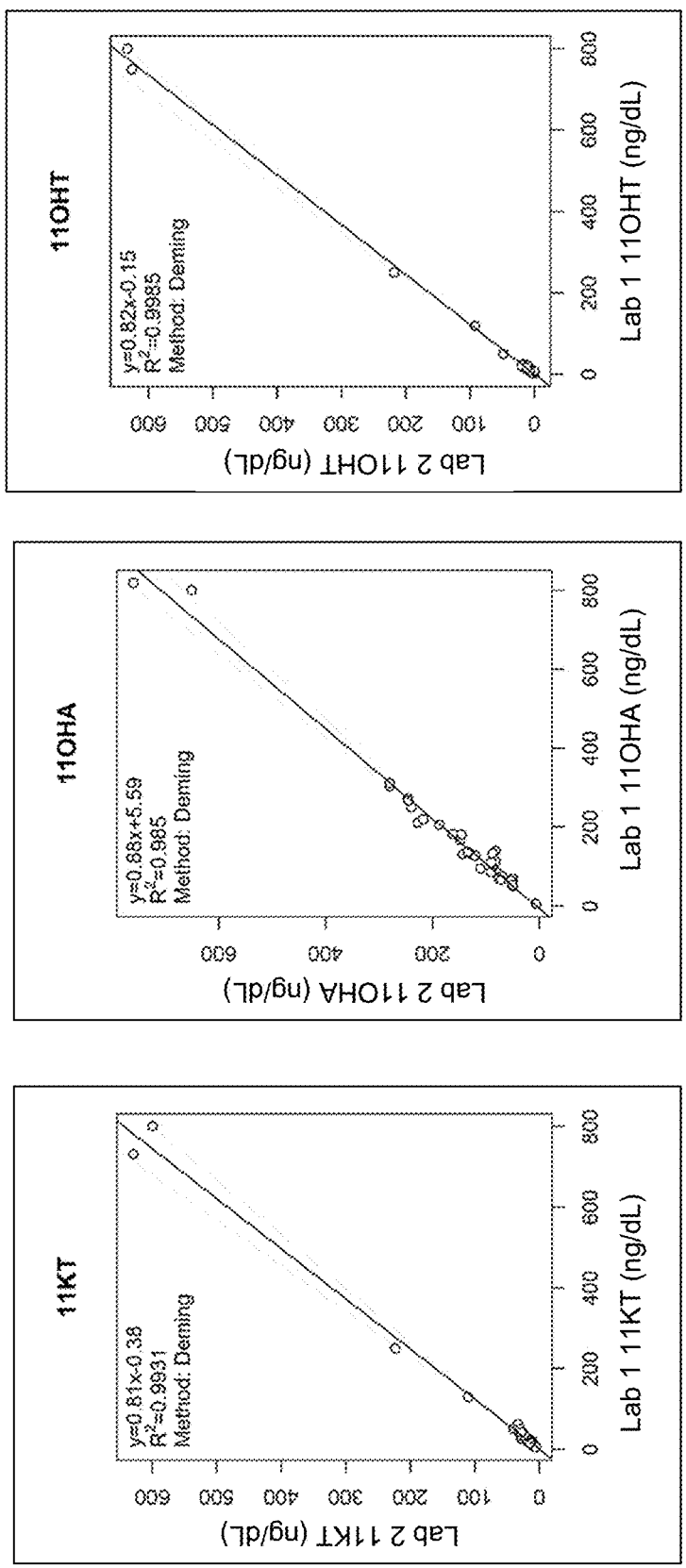

FIG. 4 shows method correlations for 11-ketotestosterone, 11-hydroxytestosterone, and 11-hydroxy$\Delta_4$androstenedione in accordance with one embodiment of the present disclosure.

Figure 5:
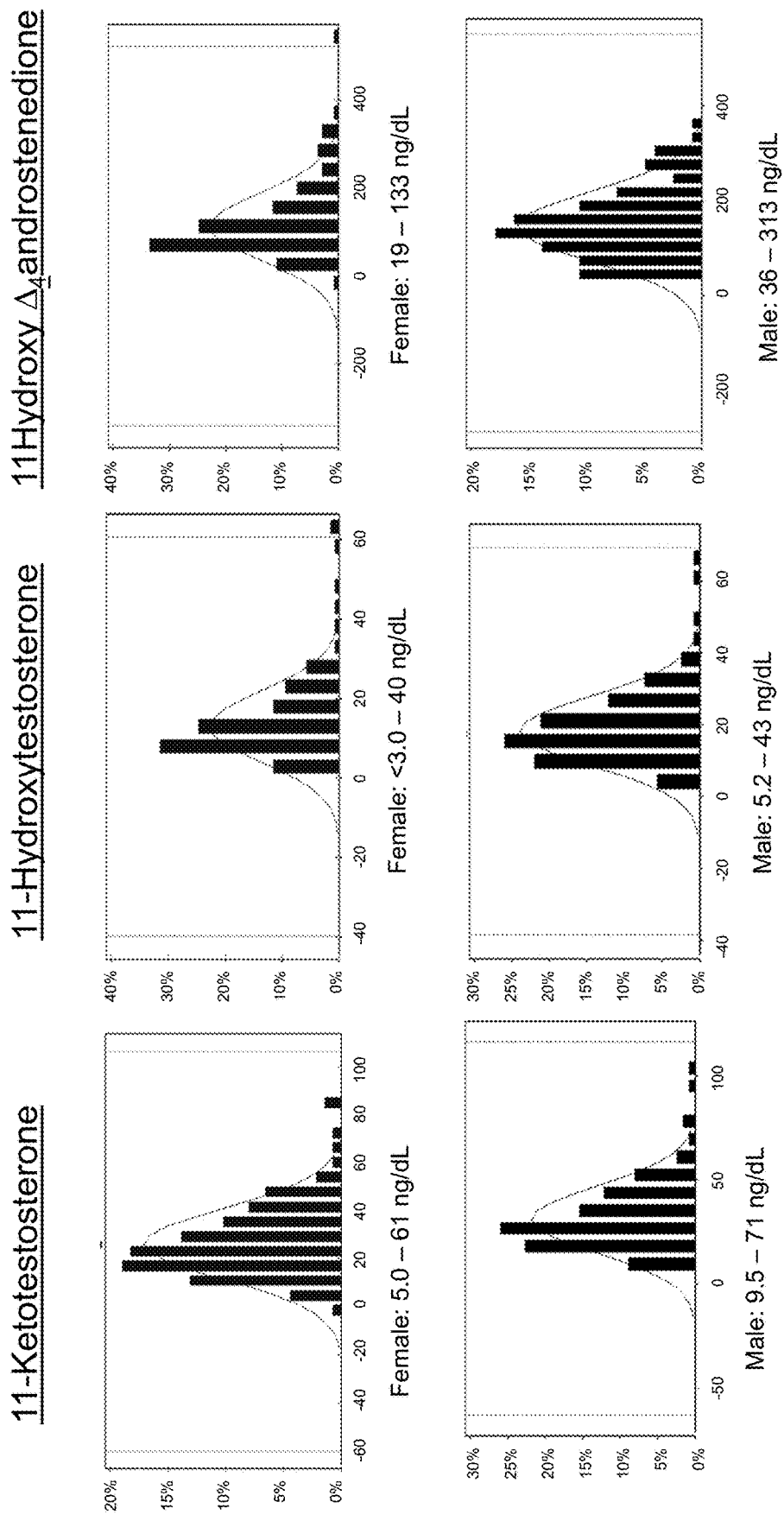

FIG. 5 shows reference intervals for 11-ketotestosterone (11KT), 11-hydroxytestosterone (11OHA), and 11-hydroxy$\Delta_4$androstenedione (11OHT) in males and females in accordance with one embodiment of the present disclosure.

DETAILED DESCRIPTION

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Definitions

While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

The term "accuracy" refers to closeness of the agreement between a test result and the accepted reference value expressed as absolute and/or relative bias.

The term "analyte" refers to a compound being measured or detected and/or component represented in the name of a measurable quantity.

The term "analytical measurement range" (AMR) refers to the range of analyte values that a method can directly measure on the specimen without any dilution, concentration, or other pretreatment not part of the usual assay process.

The term "analytic interferences" refers to an artifactual increase or decrease in apparent concentrations, activity, or intensity of an analyte due to the presence of a substance that reacts specifically or nonspecifically with either the detection reagent or the signal itself.

The term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample.

The term "biomarker" is any biomolecule that may provide biological information about the physiological state of an organism. In certain embodiments, the presence or absence of the biomarker may be informative. In other embodiments, the level of the biomarker may be informative.

The term "specificity" refers to the ability of the measurement procedure to discriminate the analyte of interest when presented with substances potentially found within a sample. In an embodiment, it is expressed as a percent (%) cross-reactivity and/or response to substances other than analyte of interest in the absence of the analyte of interest.

The term "selectivity" refers to the ability of the measurement procedure to accurately measure the analyte of interest without contribution of the substances potentially found within a sample. In an embodiment, it is expressed as a % cross-reactivity and/or response to substances other than analyte of interest in the presence of the analyte of interest.

As used herein, a "subject" may comprise an animal. Thus, in some embodiments, the sample or biological sample is obtained from a mammalian animal, including, but not limited to a dog, a cat, a horse, a rat, a monkey, and the like. In some embodiments, the sample or biological sample is obtained from a human subject. In some embodiments, the subject is a patient, that is, a living person presenting themselves in a clinical setting for diagnosis, prognosis, or treatment of a disease or condition. In some embodiments, the test sample is not a biological sample, but comprises a non-biological sample, e.g., obtained during the manufacture or laboratory analysis of a synthetic steroid, which can be analyzed to determine the composition and/or yield of the manufacturing and/or analysis process.

The terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the analyte, for example, one or more components that could interfere with detection of an analyte by mass spectrometry.

As used herein, "derivatizing" means reacting two molecules to form a new molecule. Derivatizing agents may include isothiocyanate groups, dansyl groups, dinitro-fluorophenyl groups, nitrophenoxycarbonyl groups, and/or phthalaldehyde groups.

As used herein, the term "chromatography" refers to a process in which a chemical mixture carried by a liquid or gas is separated into components as a result of differential distribution of the chemical entities as they flow around or over a stationary liquid or solid phase.

The term "Limit of Blank" (LOB) refers to the highest measurement result that is likely to be observed for a blank samples (with a stated probability). LOB is typically expressed as mean plus 1.645×SD (or 2×SD) of blank measurements.

The term "Limit of Detection" (LOD) refers to the lowest amount of analyte in a sample that can be detected (with stated probability). LOD is typically expressed as LOB plus 1.645×SD (or 2×SD) of low sample measurements.

The term "Lower Limit of Quantitation" (LLOQ) refers to the lowest amount of analyte in a sample that can be quantitatively determined with stated acceptable precision and accuracy.

The term "Upper Limit of Quantitation" (ULOQ) refers to the highest amount of analyte in a sample that can be quantitatively determined without dilution.

The term "Intra-run Imprecision" refers to the closeness of the agreement between the results of successive measurements of the same measurand carried under the same conditions of measurements (same analytical run).

The term "Inter-run Imprecision" refers to the closeness of the agreement between independent test results obtained under stipulated conditions (different analytical runs and/or operators, laboratories, instruments, reagent lots, calibrators, etc.).

The term "Maximum Dilution/Concentration" refers to the established laboratory specifications for the maximum dilution and/or concentration that may be performed to obtain a reportable numeric result.

The term "Reference Interval" refers to an interval that, when applied to the population serviced by the laboratory, correctly includes most of the subjects with characteristics similar to the reference group and excludes the others.

As used herein, "liquid chromatography" (LC) refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC). As used herein, the term "HPLC" or "high performance liquid chromatography" refers to liquid chromatography in which the degree of separation is increased by forcing the mobile phase under pressure through a stationary phase, typically a densely packed column.

The chromatographic column typically includes a medium (i.e., a packing material) to facilitate separation of chemical moieties (i.e., fractionation). The medium may include minute particles. The particles can include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytyptic (i.e. mixed) mode.

As used herein, "high turbulence liquid chromatography" or "HTLC" or "turbulent flow liquid chromatography" or "TFLC" analysis relies on column packings in which turbulent flow of the sample through the column is the basis for separation of the analyte of interest from the sample. In such columns, separation is a diffusional process. Turbulent flow, such as that provided by HTLC columns and methods, may enhance the rate of mass transfer, improving the separation characteristics provided. For example, in a typical high turbulence or turbulent liquid chromatography system, the sample may be injected directly onto a narrow (e.g., 0.5 mm to 2 mm internal diameter by 20 to 50 mm long) column packed with large (e.g., >25 micron) particles. When a flow rate (e.g., 3-500 mL per minute) is applied to the column, the relatively narrow width of the column causes an increase in the velocity of the mobile phase. The large particles present in the column can prevent the increased velocity from causing back pressure and promote the formation of vacillating eddies between the particles, thereby creating turbulence within the column.

In high turbulence liquid chromatography, the analyte molecules can bind quickly to the particles and typically do not spread out, or diffuse, along the length of the column. This lessened longitudinal diffusion typically provides better, and more rapid, separation of the analytes of interest from the sample matrix. Further, the turbulence within the column reduces the friction on molecules that typically occurs as they travel past the particles. For example, in traditional HPLC, the molecules traveling closest to the particle move along the column more slowly than those flowing through the center of the path between the particles. This difference in flow rate causes the analyte molecules to spread out along the length of the column. When turbulence is introduced into a column, the friction on the molecules from the particle is negligible, reducing longitudinal diffusion.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

As used herein, the terms "mass spectrometry" or "MS" generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, "tandem mass spectrometry" (MS/MS) is used. See, e.g., U.S. Pat. No. 6,107,623, entitled "Methods and Apparatus for Tandem Mass Spectrometry," which is hereby incorporated by reference in its entirety. Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter (quadrupole 1 or Q1) to select those ions having a particular mass-to-charge ratio. These ions are then fragmented, typically by collisions with neutral gas molecules in the second quadrupole (Q2), to yield product (fragment) ions which are selected in the third quadrupole (Q3), the mass spectrum of which is recorded by an electron multiplier detector. The product ion spectra so produced are indicative of the structure of the precursor ion, and the two stages of mass filtering can eliminate ions from interfering species present in the conventional mass spectrum of a complex mixture.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique. The term "chemical ionization" as used herein refers to methods in which a reagent gas (e.g. ammonia) is subjected to electron impact, and analyte ions are formed by the interaction of reagent gas ions and analyte molecules. The term "field desorption" as used herein refers to methods in which a non-volatile test sample is placed on an ionization surface, and an intense electric field is used to generate analyte ions.

The term "desorption" as used herein refers to the removal of an analyte from a surface and/or the entry of an analyte into a gaseous phase.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+(see e.g., Robb et al., 2000, Anal. Chem. 72(15): 3653-3659).

The term "inductively coupled plasma" as used herein refers to methods in which a sample is interacted with a partially ionized gas at a sufficiently high temperature to atomize and ionize most elements.

As used herein, the term "on-line" refers to purification or separation steps that are performed in such a way that the test sample is disposed, e.g., injected, into a system in which the various components of the system are operationally connected and, in some embodiments, in fluid communication with one another.

In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

As used herein, the term "immunoassay" (IA) refers to a method for measuring the amount of an analyte of interest by quantifying the binding, or the inhibition of binding, of a substance to an antibody. Where an enzyme is used to detect the amount of binding of the substance (e.g. antigen) to an antibody, the assay is an enzyme-linked immunoassay (ELISA). As used herein, the term "radioimmunoassay" (RIA) refers to a method for measuring the amount of an analyte of interest by quantifying the binding, or the inhibition, of binding, of a radiolabled substance to an antibody.

As used herein, the term "hemolysed" refers to the rupturing of the red blood cell membrane, which results in the release of hemoglobin and other cellular contents into the plasma or serum and the term "lipemic" refers to an excess of fats or lipids in blood.

Methods and Systems for the Analysis of 11-Oxo Androgens by LC-MS

Embodiments of the disclosure include methods and systems for the quantitative analysis of 11-oxo androgens as endogenous biomarkers. The measurement of these biomarkers may be used for clinical diagnosis. In an embodiment, the disclosed methods and systems allow for measurement of such hormones without the need for derivatation processes. In certain embodiments, the test samples suitable for analysis by the methods and systems of the disclosure can include any liquid sample that can contain one or more target analytes of interest. In an embodiment, the biomarker is endogenous to a subject. For example, in some embodiments, the test sample comprises a biological sample. The present invention may be embodied in a variety of ways.

Methods

In one embodiment, the disclosure comprises a method for determining the presence or amount of at least one 11-oxo androgen of interest in a sample, the method comprising: providing a sample believed to contain at least one 11-oxo androgen biomarker of interest; chromatographically separating the at least one 11-oxo androgen biomarker of interest from other components in the sample; and analyzing the chromatographically separated at least one 11-oxo androgen biomarker of interest by mass spectrometry to determine the presence or amount of the at least one biomarker of interest in the sample. In some embodiments, the biological sample is a biological sample obtained from a human or another mammal.

In certain embodiments, the 11-oxo androgen may comprise at least one of 11-hydroxyandrostendione (11OHA), 11-hydroxytestosterone (11OHT) or 11-ketotestosterone (11KT). As used herein, 11-hydroxyandrostendione (11OHA) refers to 11-hydroxy $\Delta_4$androstendione.

For example, in one embodiment, disclosed is a method for determining the presence or amount of at least one 11-oxo androgen in a biological sample by tandem mass spectrometry. The method may comprise any one of the steps of: (a) obtaining a biological sample from a subject; (b) optionally adding a stable isotope-labeled 11-oxo androgen to the biological sample as an internal standard; (c) optionally performing liquid-liquid extraction; (d) performing HPLC; and (e) measuring the 11-oxo androgen (both labeled and unlabeled) by mass spectrometry. In an embodiment, the mass spectrometry is tandem mass spectrometry (MS/MS). For example, in one embodiment, the tandem MS/MS spectrometry comprises use of a triple quadrupole tandem mass spectrometer.

In an embodiment, the tandem mass spectrometry may comprise the steps of: (i) generating a precursor ion of the 11-oxo androgen; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the 11-oxo androgen in the sample. In certain embodiments, the tandem mass spectrometry uses positive ion atmospheric pressure chemical ionization (APCI) mode. Also, in certain embodiments, quantification of the analyte of interest and the optional internal standard is performed in selected reaction monitoring mode (SRM).

In an embodiment, the tandem mass spectrometry is coupled to HPLC. The HPLC step may directly precede the tandem mass spectrometry analysis (i.e., LC-MS/MS). In some embodiments, the HPLC is high turbulence liquid chromatography (HTLC). In certain embodiments, the sample is not subjected to convergence chromatography. In some embodiments, the LC is not ulta performance liquid chromatography (UPLC).

In an embodiment, the LC-MS/MS is performed on-line. For example, as disclosed herein, any one of the steps of the method may be controlled by a computer. In some embodiments, the computer comprises one or more data processors and/or a non-transitory computer readable storage medium containing instructions (e.g. software program). Thus, also disclosed herein is a non-transitory computer readable storage medium containing instructions which, when executed on one or more computers, cause the one or more computers to perform actions comprising at least one of the steps of the methods disclosed herein.

The method may, in certain embodiments, comprise the measurement of multiple m/z precursor-fragment transitions. For example, in certain embodiments, and as explained in more detail herein, a first fragment is selected for quantitation of the 11-oxo androgen of interest, whereas an additional fragment or fragments may be chosen as a qualitative standard(s).

For example, for 11-hydroxyandrostendione (11OHA), transitions of a precursor of 303.401 m/z to fragments of 121.150, 121.100, 121.050 m/z (echo peaks) with qualifier fragment peaks of 105.100 and/or 97.100 m/z may be measured. Or, the m/z fragment of 121.100 may be measured. For the internal standard $^2H_4$-11β-hydroxyandrostenedione, the precursor ion may be 308.400 m/z and the fragment may be 122.200 m/z. For the internal standard qualifier peak, the precursor may be 307.400 m/z and the fragment may be 109.200 m/z.

For 11-ketotestosterone (11KT), transitions of a precursor of 303.400 m/z to fragments of 121.200, 121.150, or 121.250 m/z, with qualifier fragment peaks of 105.200 and/or 91.200 m/z may be measured. Or, the m/z fragment of 121.200 may be measured. For the internal standard $^2H_3$-11β-ketotestosterone, the precursor ion may be 306.400 m/z and the fragment may be 121.20 m/z.

For 11-hydroxytestosterone (11OHT), transitions of a precursor of 305.400 m/z to fragments of 121.100, 121.150, or 121.050 m/z, with qualifier fragment peaks of 105.000 and/or 97.000 m/z may be measured. Or, the m/z fragment of 121.100 may be measured. For the internal standard $^2H_4$-11β-hydroxytestosterone, the precursor ion may be 309.200 m/z and the fragment may be 121.100 m/z. For internal standard qualifier peaks of $^2H_4$-11β-hydroxytestosterone, the precursor may be 309.200 m/z and the fragment may be 109.100 and/or 97.100 m/z.

In some embodiments, the methods of the disclosure comprise at least partial purification of the 11-oxo androgen of interest prior to LC-MS/MS. In some embodiments, the methods may comprise at least one purification step, such as protein precipitation, liquid-liquid extraction (LLE), solid phase extraction (SPE), immunopurification, and any combination thereof. In certain embodiments, the sample is subjected to an extraction column. In an embodiment, the column is a LLE column. In an embodiment, the LLE may comprise the use of hexane:ethylacetate. Or, in some embodiments, the column is a SPE column. In some instances, the extraction and mass spectrometry are performed on-line. The method may also include sample dilution prior to analysis by LC-MS/MS. The partial purification may also comprise dilution. In some embodiments, duplicate sets of charcoal stripped calibrators are analyzed in each batch and the back-calculated amount of the individual analyte in the sample determined from calibration curves generated by spiking known amounts of each purified analyte into charcoal stripped serum to generate a final concentration of purified analyte of interest that is within the range of about 3.0 to 1,000 ng/dL.

An example of a method (2) of the present invention is shown in FIG. 1. Thus, in an embodiment, the method may include a step of providing a sample, for example, a serum sample believed to contain one or more 11-oxo androgens of interest (4). In some embodiments, an appropriate internal standard is added to the sample (6). For example, in some embodiments of the presently disclosed method for analyzing an 11-oxo androgen in serum samples, at least one of $^2H_3$-11β-ketotestosterone, $^2H_4$-11β-hydroxytestosterone and/or $^2H_4$-11β-hydroxyandrostenedione (commercially available from King of Prussia, Pa.) is added as an internal standard for the measurement of 11KT, 11OHT and 11OHA, respectively. Or, other stable labeled isotopes of 11KT, 11OHT or 11OHA may be used.

In yet other embodiments, structural analogues of the 11-oxo androgen biomarker of interest may be used. For example, such structural analogues may comprise compounds wherein a first chemical group is replaced with a second chemical group. In general, the groups are of similar chemical reactivity, but different mass, as for example, the replacement of a methyl (—CH$_3$) group with an ethyl (—CH$_2$CH$_3$) group.

In some embodiments, the analytes of interest are partially purified by LLE of the sample (8) prior to HPLC. Additionally and/or alternatively, the sample may be diluted in a solvent that can be used for LC or MS in subsequent purification steps.

In an embodiment, the LLE is used to concentrate and partially purify the analyte. For example, the LLE may remove lipids and/or fibrinogen from the biological samples. In some embodiments, an 11-oxo androgen can be extracted from a serum sample with an organic solvent. For example, in an embodiment, an alkane mixed with a more polar solvent is used. For example, in certain embodiments, hexane is mixed with a more polar solvent. In an embodiment, the polar solvent comprises ethyl acetate or a similar solvent. In an embodiment, 9:1 hexane:ethyl acetate is used. Or, other solvents may be used. After LLE, the sample can be centrifuged (e.g., 2000 rpm or 1207 g) for about 1 minute, the supernatant decanted, and the pelleted sample evaporated to remove residual solvent and then reconstituted in a solvent appropriate for LC or HPLC (e.g., acetonitrile: water).

Still referring to FIG. 1, the method may further include liquid chromatography (9) as a means to separate the analyte of interest from other components in the sample. In an embodiment, two liquid chromatography steps are used. For example, the method may comprise a first extraction column liquid chromatography followed by transfer of the biomarker of interest to a second HPLC analytical column. In other embodiments, only one HPLC step is used.

For example, the reconstituted extract may be applied onto a HPLC system, wherein the analytes are eluted using an isocratic separation through an extraction column. In certain embodiments, the mobile phase that is used comprises a gradient.

The liquid chromatography may, in certain embodiments, comprise high turbulence liquid chromatography or high throughput liquid chromatography (HTLC) (sometimes refreerd to as turbulent flow liquid chromatography (TFLC). See, e.g., Zimmer et al., J. Chromatogr. A 854:23-35 (1999); see also, U.S. Pat. Nos. 5,968,367; 5,919,368; 5,795,469; and 5,772,874. In some embodiments, HTLC, alone or in combination with one or more purification methods, may be used to purify the biomarker of interest prior to mass spectrometry. Also, in some embodiments, the use of a HTLC sample preparation method can eliminate the need for other sample preparation methods including liquid-liquid extraction. Thus, in some embodiments, the test sample, e.g., a biological fluid, can be disposed, e.g., injected, directly onto a high turbulence liquid chromatography system.

For example, in one embodiment, an Aria TX4 HTLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used. In this embodiment, the sample is reconstituted in 10% acetonitrile in reagent grade water prior to application to the HTLC column. In an embodiment, the Pump A mobile phase is acetonitrile:methanol:water (5:5:90) and the Pump B mobile phase is acetonitrile:methanol:water (45:45:10).

The separated analytes are then introduced into a mass spectrometer (MS) system (10). In some embodiments, a tandem MS/MS system is used. In an embodiment, an API 5000 or API 5500 (or equivalent) Tandem Mass Spectrometer, Danaher (Toronto, Calif.) is used. The analyte of interest may then be quantified based upon the amount of the characteristic transitions measured by tandem MS as detailed herein. In some embodiments, the tandem mass spectrometer comprises a triple quadrupole mass spectrometer.

In mass spectrometry, analytes are ionized to produce gas phase ions suitable for resolution in the mass analyzer. Ionization occurs in the ion source. There are several ion sources known in the art. In some embodiments, the analyte may be ionized by any method known in the art. For example, ionization may be performed using any of the following ion sources: atmospheric pressure chemical ionization (APCI), atmospherice pressure photoionization (APPI), electron impact ionization (EI), electrospray ionization (ESI), matrix assisted laser desorption (MALDI), surface enhanced laser desorption ionization (SELDI), thermospray ionization, inductively coupled plasma (ICP), and fast atom bombardment (FAB). 11-oxo androgens may be ionized in positive or negative ion mode.

In certain embodiments, the tandem mass spectrometer is operated in a positive ion atmospheric pressure chemical ionization (APCI) mode. In some embodiments, the quantification of the analytes and internal standards is performed in the selected reaction monitoring mode (SRM).

In some embodiments, the back-calculated amount of each analyte in each sample may be determined by comparison of the sample response or response ratio when employing internal standardization to calibration curves generated by spiking a known amount of purified analyte material into a standard test sample, e.g., charcoal stripped human serum. In one embodiment, calibrators are prepared at known concentrations to generate a response or response ratio when employing internal standardization versus concentration calibration curve. In an embodiment, this determination is performed at least in part by a computer or data analysis system and/or a non-transitory computer readable storage medium containing instructions which, when executed on the one or more data processors, cause the one or more data processors to perform actions to make this determination.

In various embodiments, the method includes a detailed review of raw data, quality control, review and interpretation of patient results followed by release to the laboratory system. For example, in certain embodiments, duplicate calibration curves are used for each batch of samples. A total of 25% of standard points may be excluded from the combined curves if the back-calculated concentrations exceed the theoretical concentrations by >20% at the LLOQ or >15% at other concentrations. In an embodiment, a result may be reported below the lowest, or above the highest remaining standard. In an embodiment, the standard curve correlation coefficient is (r)>0.98. Also, in certain embodiments, control pools must be within acceptable limits as is known in the art. For example, in certain embodiments, four levels of controls may be selected for 11KT, 11OHT, and 11OHA. In some embodiments, the control data are recorded for each run on Levy-Jennings charts. The control chart may be reviewed for shifts or trends. All chromatographic peak shapes may be reviewed for consistency. For example, where peak distortion is observed; a contaminant may be present. In an embodiment, the method includes ensuring that the correct peak is integrated where multiple peaks are observed within the chromatogram by confirming that the retention time of the peak integrated corresponds to calibrators and quality control samples. For example, the method may include review of the internal standard peak area vs. index plot. In an embodiment, internal standard peak areas more than 50% greater than the neighboring peaks may be submitted for repeat analysis and/or internal standard peak areas more than 33% less than the neighboring peaks may be submitted for repeat analysis. In an embodiment, this review and analysis is done by a computer or data analysis system and/or a non-transitory computer readable storage medium containing instructions, which when executed on the one or more data processors, cause the one or more data processors to perform actions to perform this analysis and/or review.

Systems for the Analysis of 11-Oxo Androgens

In other embodiments, disclosed is a system for determining the presence or amount of one or more 11-oxo androgen biomarkers in a sample. For example, in some embodiments the system may comprise: a station for providing a sample believed to contain at least one 11-oxo androgen biomarker of interest; a station for chromatographically separating the at least one 11-oxo androgen biomarker of interest from other components in the sample; and a station for analyzing the chromatographically separated at least one 11-oxo androgen biomarker of interest by mass spectrometry to determine the presence or amount of the one or more biomarkers in the sample. In an embodiment, the sample is a biological sample obtained from a human or another mammal.

In an embodiment, the mass spectrometry is tandem mass spectrometry (MS/MS). In an embodiment, the mass spectrometry is operated in an atmospheric pressure chemical ionization (APCI) mode. In an embodiment, quantification of the 11-oxo androgen biomarker of interest is performed in selected reaction monitoring mode (SRM). For example, the station for tandem mass spectrometry may comprise an Applied Biosystems API5000 or API5500 tandem mass spectrometer (or equivalent), Danaher (Toronto, Calif.).

In one embodiment, the station for chromatographic separation comprises at least one apparatus to perform liquid chromatography (LC). In one embodiment, the station for liquid chromatography comprises a column for extraction chromatography. Additionally or alternatively, the station for liquid chromatography comprises a column for analytical chromatography. In certain embodiments, the column for extraction chromatography and analytical chromatography comprise a single station or single column. Various columns comprising stationary phases and mobile phases that may be used for extraction or analytical liquid chromatography are described herein. A column used for extraction liquid chromatography may be varied depending on the biomarker of interest. In some embodiments, the extraction column is a functionalized silica or polymer-silica hybrid or polymeric particle or monlithic silica stationary phase, such as a Poroshell SBC-18 column. A column used for analytical liquid chromatography may be varied depending on the biomarker of interest and/or the column that was used for the extraction liquid chromatography step. For example, in certain embodiments, the analytical column comprises particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

In some embodiments, HPLC is used to purify the 11-oxo androgens from other components in the sample that co-purify with the 11-oxo androgens after extraction and/or dilution of the sample. In an embodiment, HTLC is used to purify the 11-oxo androgens from other components in the sample. For example, in one embodiment, an Aria TX4 HPLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used.

In an embodiment, the system may further comprise a station for partially purifying the at least one 11-oxo androgen biomarker of interest from other components in the sample as for example by liquid-liquid extraction (LLE) and/or dilution. Or, in some embodiments, solid phase extraction (SPE) may be used. Thus, in certain embodiments, the system may also comprise a station for extracting the one or more 11-oxo androgen biomarkers from the test sample and/or diluting the sample. The station for partial purification (e.g., LLE) may comprise equipment and reagents for addition of solvents to the sample and removal of waste fractions. In some cases a isotopically-labeled internal standard such as $^2H_3$-11β-ketotestosterone, $^2H_4$-11β-hydroxytestosterone and/or $^2H_4$-11β-hydroxyandrostenedione (commercially available from King of Prussia, Pa.) is used to standardize losses of the biomarker that may occur during the procedures. Thus, the station for LLE may comprise a hood or other safety features required for working with solvents.

Also, in certain embodiments, at least one of the stations is automated and/or controlled by a computer. For example, as described herein, in certain embodiments, at least some of the steps are automated such that little to no manual intervention is required. For example, as disclosed herein, any one of the stations may be controlled by a data processor or a computer. Also disclosed herein is a data processor and/or a non-transitory computer readable storage medium containing instructions which, when executed on the one or more data processors or computers, cause the one or more data processors or computers to perform actions for at least one of the stations of the system.

FIG. 2 shows an embodiment of a system (100) of the present invention. As shown in FIG. 2, the system may comprise a station for aliquoting a sample (104) that may comprise a biomarker (e.g., one or more 11-oxo androgens) of interest into sampling containers. In one embodiment, the sample is aliquoted into a container or containers to facilitate liquid-liquid extraction or sample dilution. The station for aliquoting may comprise receptacles to discard the portion of the sample that is not used in the analysis.

The system may further comprise a station for adding an internal standard to the sample (108). In an embodiment, the internal standard comprises the biomarker (e.g., one or more 11-oxo androgens) of interest labeled with a non-natural isotope. Thus, the station for adding an internal standard may comprise safety features to facilitate adding an isotopically labeled internal standard solutions to the sample. The system may also, in some embodiments, comprise a station (110) for LLE and/or dilution of the sample.

The system may also comprise a station for liquid chromatography (LC) of the sample (112). As described herein, in an embodiment, the station for liquid chromatography may comprise an extraction liquid chromatography column, or the station may comprise HPLC and no extraction column. Or, as discussed in more detail below, other types of liquid chromatography, such as high turbulence liquid chromatography (HTLC) may be used. For example, in one embodiment, an Aria TX4 HTLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used. In this embodiment, the sample may be reconstituted in 10% acetonitrile in reagent grade water prior to application to the HTLC column. In an embodiment, the Pump A mobile phase is acetonitrile:methanol:water (5:5:90) and the Pump B mobile phase is acetonitrile:methanol:water (45:45:10).

Thus, the station for liquid chromatography may comprise a column comprising the stationary phase, as well as containers or receptacles comprising solvents that are used as the mobile phase. The station may comprise the appropriate lines and valves to adjust the amounts of individual solvents being applied to the column or columns. Also, the station may comprise a means to remove and discard those fractions from the LC that do not comprise the biomarker of interest. In an embodiment, the fractions that do not contain the biomarker of interest are continuously removed from the column and sent to a waste receptacle for decontamination and to be discarded.

Also, the system may comprise a station for characterization and quantification of the 11-oxo-androgen(s) of interest. In one embodiment, the system may comprise a station for mass spectrometry (MS) of the 11-oxo-androgen biomarker(s) (116). In an embodiment, the station for mass spectrometry comprises a station for tandem mass spectrometry (MS/MS). Also, the station for characterization and quantification may comprise a station for data analysis (118). The station for data analysis may be part of the MS/MS station or a separate station and may comprise a computer and/or software for analysis of the MS/MS results. In an embodiment, the station for data analysis comprises a computer or data processor and/or a non-transitory computer readable storage medium (e.g., software) containing instructions, which when executed on the one or more data processors, cause the one or more data processors to perform the data analysis. In an embodiment, the analysis comprises both identification and quantification of the biomarker of interest.

In some embodiments, one or more of the purification or separation steps can be performed "on-line." The on-line system may comprise an autosampler for removing aliquots of the sample from one container and transferring such aliquots into another container. For example, an autosampler may be used to transfer the sample after extraction onto an LC extraction column. The on-line system may comprise one or more injection ports for injecting the fractions isolated from the LC extraction columns onto the LC analytical column and/or one or more injection ports for injecting the LC purified sample into the MS system. Thus, the on-line system may comprise one or more columns, including but not limited to an HTLC column. In such "on-line" systems, the test sample and/or analytes of interest can be passed from one component of the system to another without exiting the system, e.g., without having to be collected and then disposed into another component of the system.

In some embodiments, the on-line purification or separation method is highly automated. In such embodiments, the steps can be performed without the need for operator intervention once the process is set-up and initiated. For example, in one embodiment, the system, or portions of the system may be controlled by a computer (102). Thus, in certain embodiments, the system may comprise software for controlling the various components of the system, including pumps, valves, autosamplers, and the like. Such software can be used to optimize the extraction process through the precise timing of sample and solute additions and flow rate.

Although some or all of the steps in the method and the stations comprising the system may be on-line, in certain embodiments, some or all of the steps may be performed "off-line."

Thus, the disclosure provides methods and systems for applying liquid chromatography and mass spectrometry as a means to separate a biomarker analyte of interest, such as 11-oxo androgens, from other components that may be present in a sample. The methods and systems may comprise an off-line liquid-liquid extraction and/or sample dilution step as a means to partially purify the sample prior to HTLC and tandem mass spectrometry. The methods and systems may be used for clinical diagnosis.

The systems and methods may, in certain embodiments, provide for a multiplexed assay. For example, certain embodiments of the present invention may comprise a multiplexed liquid chromatography tandem mass spectrometry (LC-MS/MS) or two-dimensional or tandem liquid chromatography-tandem mass spectrometry (LC)-LC-MS/MS) methods for the quantitative analysis of one or more 11-oxo androgens in samples.

Embodiments may provide certain advantages. In an embodiment, an accurate, precise, simple and fast HPLC-MS/MS isotope dilution commercially available method has been developed to allow quantitative measurements of 11-Ketotestosterone, 11-Hydroxytestosterone, and 11-Androstenedione in serum. The method conserves serum samples by multiplexing the analysis of the three 11-oxygenated androgens. Reference intervals can be developed for adult men and adult women. The similar distributions for men and women highlight the adrenal origin of the 11-oxyandrogens. Also, in an embodiment, good correlation with other assay systems will allow result interpretation for disease states of congenital adrenal hyperplasia, polycystic ovarian syndrome, and prostate cancer using published data.

In certain embodiments, the methods and systems may provide greater sensitivity than the sensitivities previously attainable for many of the analytes being measured. Also, embodiments of the methods and systems may provide for rapid throughput that has previously not been attainable for many of the analytes being measured.

As another advantage, the specificity and sensitivity provided by the disclosed methods and systems may allow for the analysis of analytes from a variety of materials. For example, the disclosed methods can be applied to the quantification of analytes of interest in complex sample matrices, including, but not limited to, blood, plasma, urine, saliva, and the like. Also, using the disclosed methods and systems allows for measurement of 11-oxo androgens without derivatization and at levels as low as 1-3 ng/dL. Thus, the methods and systems are suitable for clinical applications and/or clinical trials.

As additional potential advantages, in certain embodiments, the disclosed systems and methods provide approaches for addressing isobaric interferences, varied sample content, including hemolysed and lipemic samples, while attaining low ng/dL limits of quantification (LLOQ) of the target analytes. Accordingly, embodiments of the disclosed methods and systems may provide for the quantitative, sensitive, and specific detection of clinical biomarkers used in clinical diagnosis.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1—Validation of LC-MS/MS for 11-Oxo Androgens

An analytical method was developed using a TX-4 HPLC system (Thermo-Fisher) with Agilent® 1200 pumps (Agilent Technologies, Inc.) and a Sciex® 5000 (Danaher) triple quadrupole mass spectrometer. Independent calibration curves were prepared for each analyte in depleted serum (Golden West Biologicals). Sample preparation consisted of isotope dilution using a cocktail of three deuterated heavy isotope internal standards (IsoSciences) followed by LLE. A reversed phase C8 analytical column (3.0×50 mm, 2.7 um) was used with a water/methanol/acetonitrile solvent gradient to achieve chromatographic separation of all isobars in under 4 minutes. Positive mode atmospheric pressure chemical ionization (APCI) was used for detection in multiple reaction monitoring (MRM) mode. MRM is the application of SRM to multiple product ions from one or more precursor ions.

Validation Data

Analytical sensitivity was between 1-3 ng/dL for each analyte and the analytical measurement range was up to 1,000 ng/dL (up to 10,000 ng/dL with dilution). Inter-assay precision ranged from 4.6-14.9% CV for 11-ketotestosterone (11KT) at LLOQ, 6.4-13.4% CV for 11-hydroxyandrostenedione (11OHA) at LLOQ and 6.1-10.7% for 11-hydroxytestosterone (11OHT) at LLOQ. Accuracy ranged from 100.7-106.4% for 11KT, 99.3-113% for 11OHA and 98.5-101% for 11OHT. Reference intervals for both female and male adults were developed for 11KT (Female, 5.0-60.6 ng/dL; Male 9.5-70.8 ng/dL), 11OHA (Female, 19.2-333 ng/dL; Male, 36.4-313 ng/dL) and 11OHT (Female, <39.8 ng/dL; Male, 5.2-43.4 ng/dL).

A summary of the results for validation of the disclosed methods and systems is shown in Table 1.

TABLE 1

| | |
|---|---|
| Units of measure to report | ng/dL |
| ULOQ value | 1000 |
| LLOQ value | 1.0 (11KT, 11OHT) and 3.0 (11OHA) |
| AMR (Analytical Measurement Range to actually be used in production) | 3.0 to 1000 ng/dL |
| Dilution limit | 1/10 |
| Minimum/Maximum Concentrations | 3.0 ng/dL/10,000 ng/dL |
| Primary sample type used | Human serum |

Example 2—Accuracy and Precision 11-ketotestosterone, 11-hydroxytestosterone, and 11-hydroxyandrostenedione were analyzed by LC-MS/MS after isotope dilution with $d_3$-11-ketotestosterone, $d_4$-11-hydroxytestosterone and $d_4$-11-hydroxyandrostenedione (d=deuterium), respectively. Analytes and internal standards were extracted from serum samples, standards and assay controls using a hexane:ethylacetate solution. The organic fraction was separated from the aqueous layer and evaporated to dryness. Reconstituted samples, standards, and controls were transferred to a 96-well plate and analyzed by LC-MS/MS using an ARIA TX4 HPLC system and SCIEX API 5000 or 5500 mass spectrometer. The analytical measurement range of the assay is from 3.0 ng/dL to 1000 ng/dL when using a 0.5 mL sample volume. An example mass chromatogram is shown in FIG. 3.

| | |
|---|---|
| 11KT | 11-ketotestosterone |
| 11OHA | 11-hydroxyandrostenedione |
| 11OHT | 11-hydroxytestosterone |
| AMR | Analytical Measurement Range |
| CV | Coefficient of Variation |
| LC | Liquid Chromatography |
| LLOQ | Lower Limit of Quantitation |
| MS/MS | Tandem Mass Spectrometry |
| SD | Standard Deviation |
| SOP | Standard Operating Procedure |
| ULOQ | Upper Limit of Quantitation |

Working stock was prepared from commercially available purified 11KT, 11OHT and 11OHA weighed out from powder dissolved in ethanol and diluted to working standard concentrations of 1.0 to 1000 ng/dL in charcoal stripped serum.

Both bioanalytical and clinical assay quality control pools (n=25) were used as typically performed in validation. Controls for each of 11KT, and 11OHA and OHT were prepared in standard matrix and/or human serum. 11-Ketotestosterone met clinical acceptance criteria according to standard operation procedure in all 25 assays, 11-Hydroxyandrostenedione met clinical acceptance criteria in 22 of 25 assays, and 11-Hydroxytestosterone met clinical acceptance criteria in 24 of 25 assays.

Accuracy was determined by spiking a calculated volume of solution containing known concentrations of 11KT, 11OHT, and 11OHA into charcoal stripped serum. Twenty replicates of each stripped serum sample were measured in one assay to determine intra-assay accuracy and imprecision. Two replicates were measured in each additional assay run for a total of 24 replicates to determine inter-assay accuracy and imprecision.

Accuracy: Intra-assay and inter-assay accuracy to be 85-115% (80-120% at the LLOQ) and imprecision (% CV) will be ≤15% (20% at the LLOQ).

For 11KT, the intra-assay accuracy at the concentration of 1.0 ng/dL was 107.7% and the imprecision was 10.0% CV. The intra-assay accuracy at the other levels ranged from 101.1% to 104.7% and the intra-assay imprecision ranged from 3.5 to 5.9% CV.

For 11OHA, the intra-assay accuracy at the concentration of 1.0 ng/dL was 113.5% and the imprecision was 19.9%. The intra-assay accuracy at the other levels ranged from 97.8 to 103.7% and the intra-assay imprecision ranged from 5.5 to 11.2% CV.

For 11OHT, the intra-assay accuracy at the concentration of 1.0 ng/dL was 110.9% and the imprecision was 19.4% CV. The intra-assay accuracy at other levels ranged from 101.1 to 103.7% and the intra-assay imprecision ranged from 3.7 to 8.9% CV.

For 11KT, the inter-assay accuracy at the concentration of 1.0 ng/dL was 106.4% and the imprecision was 17.9% CV. The inter-assay accuracy at the other levels ranged from 100.7 to 102.8% and the inter-assay imprecision ranged from 4.1 to 9.4% CV.

For 11OHA, the inter-assay accuracy at the concentration of 1.0 ng/dL was 113.0% and the imprecision was 21.2%. At an LLOQ of 3.0 ng/dL, the accuracy was 103.9% and the imprecision was 14.3%. The inter-assay accuracy at the other levels ranged from 99.3 to 100.6% and the inter-assay imprecision ranged from 5.8 to 6.7% CV.

For 11OHT, the inter-assay accuracy at the concentration of 1.0 ng/dL was 98.5% and the imprecision was 18.8% CV. The inter-assay accuracy at other levels ranged from 95.6 to 101.0% and the inter-assay imprecision ranged from 4.9 to 16.5% CV.

Correlations between two different testing labs are shown in FIG. 4. The Deming's regression analyses comparing LC-MS/MS results for two different testing labs (Lab 1 and Lab 2) showed slopes that were between 0.81 and 0.88 (FIG. 4). The Deming's regression for 11KT was y=0.81x+0.38 with an $R^2$ value of 0.9931. The Deming's regression for 11OHA was y=0.88x+5.59 with an $R^2$ value of 0.985. The Deming's regression for 11OHT was y=0.82x−0.15 with an $R^2$ value of 0.9985.

Sample Matrix Imprecision Acceptance Criteria:
Intra-assay and inter-assay imprecision (% CV) is ≤15%.
For 11KT, the intra-assay imprecision ranged from 2.4 to 4.2% CV. For 11OHA, the intra-assay imprecision ranged from 2.9 to 7.8% CV. For 11OHT, the intra-assay imprecision ranged from 2.5 to 10.9% CV.

For 11KT, the inter-assay imprecision ranged from 4.6 to 9.5% CV. For 11OHA, the inter-assay imprecision after removing the outlier data ranged from 6.0 to 13.0% CV. For 11OHT, the inter-assay imprecision ranged from 6.0 to 10.0% CV.

Example 3—Lower Limit of Quantitation

The lower limit of quantitation (LLOQ) is defined as the lowest concentration that meets acceptance criteria in both intra-assay and inter-assay accuracy (80-120%) and imprecision (≤20% CV).

Acceptance Criteria: Intra-assay and inter-assay accuracy to be 80% to 120% and % CV to be ≤20%. In addition, the chromatographic response at the LLOQ is at least 5 times the mean blank response.

For 11KT, the lowest concentration to meet the acceptance criteria for the LLOQ was 1.0 ng/dL. For 11OHA, the lowest concentration to meet the acceptance criteria for the LLOQ was 3.0 ng/dL. For 11OHT, the lowest concentration to meet the acceptance criteria for the LLOQ was 1.0 ng/dL.

For 11KT, the ratio of the mean chromatographic response and the mean blank (S0) from the intra-assay accuracy data was 23.4. The ratios of the chromatographic response and the blank (S0) from the inter-assay accuracy data ranged from 3.1 to 56.8 with a mean of 10.0.

For 11OHA, the ratio of the mean chromatographic response and the mean blank (S0) from the intra-assay accuracy data was 8.0. The ratios of the chromatographic response and the blank (S0) from the inter-assay accuracy data ranged from 4.7 to 21.8 with a mean of 9.1.

For 11OHT, the ratio of the mean chromatographic response of and the mean blank (S0) from the intra-assay accuracy data was 32.5. The ratios of the chromatographic response and the blank (S0) from the inter-assay accuracy data ranged from 5.1 to 17.8 with a mean of 8.9.

Example 4—Upper Limit of Quantitation

The upper limit of quantitation (ULOQ) is defined as the highest concentration that meets acceptance criteria in both intra-assay and inter-assay accuracy (85-115%) and imprecision (≤15% CV).

Acceptance Criteria: Intra-assay and inter-assay accuracy is 85-115% and % CV is ≤15%.

For 11KT, the highest concentration measured that met acceptance criteria was 1000 ng/dL. For 11OHA, the highest concentration measured that met the acceptance criteria was 1000 ng/dL. For 11OHT, the highest concentration measured that met acceptance criteria was 1000 ng/dL.

Example 5—Analytic Interference (Lipemia, Hemolysis and Icterus)

A high concentration pooled sample was tested for interference of lipemia, hemolysis and icterus. The high concentration sample was mixed with various volumes of serum samples with a highly lipemic sample, a sample spike to 20% (v/v) red blood cells, and a sample spiked to 16 mg/dL conjugated and 16 mg/dL un-conjugated bilirubin. Results were compared to the original neat sample.

Acceptance Criteria: Recovery of analyte to be 85-115% in at least ⅔ of the replicates for each sample at each interferent concentration. For each of 11KT, 11OHA and 11OHT all replicates at each concentration of lipemia, hemolysis, and bilirubin were within acceptance criteria. This demonstrates that these matrix components did not have an effect on the analysis of 11KT, 11OHA or 11OHT.

Example 6—Sample Type

Samples of red-top serum, SST serum, EDTA plasma and heparin plasma were collected from three volunteer donors. Each sample type was analyzed in triplicate and the individual and mean results of SST serum, EDTA plasma, and heparin plasma were compared to the red-top serum results.

Acceptance Criteria: Percent recovery of analyte compared to baseline (red-top serum) to be 85-115% for the mean result and in ⅔ replicates for each sample type.

Example 7—Selectivity in Human Serum and Standard Matrix

The selectivity of the method was demonstrated by spiking known concentrations of analyte (0, 50, 200 and 800 ng/dL) into human serum samples. The neat and spiked samples were analyzed in triplicate and the results compared to the neat mean result.

Acceptance Criteria: Recovery of analyte to be within 85-115% of the expected value (neat mean result plus spiked concentration). For each of 11KT, 11OHA and 11OHT, all replicates at each concentration were within 85-115% of the expected result.

Selectivity in standard matrix was also demonstrated by spiking charcoal stripped serum with known concentrations of analyte (0, 50, 200 and 800 ng/dL) then analyzing neat and spiked samples in triplicate with the results compared to the baseline (neat) mean concentration.

Acceptance Criteria: Recovery of analyte to be within 85-115% of the expected value (neat mean result plus spiked concentration). For each of 11KT, 11OHA and 11OHT, all replicates at each concentration were within 85-115% of the expected result.

Example 8—Internal Standard Interference

The amount of internal standard interference in the analyte transition was demonstrated by analyzing the working concentration of internal standard spiked into water, and comparing the response in the analyte transition with the low standard (1.0 ng/dL) of the assay and accuracy sample 1 (1.0 ng/dL).

Acceptance Criteria: Analyte response of the internal standard to be less than the low standard.

For 11KT, the mean contribution of the internal standard to the analyte transition was 26.6% of the response of the low standard.

For 11OHA, the mean contribution of the internal standard to the analyte transition was 9.5% of the response of the low standard.

For 11OHT, the mean contribution of the internal standard to the analyte transition was 22.3% of the response of the low standard.

Example 9—Linearity of Dilution

Linearity of dilution was demonstrated by spiking three samples to a high concentration and diluting them ½, ⅕, and ¹⁄₁₀ with reagent grade water before analyzing in triplicate. Results of dilutions were compared to neat sample.

Acceptance Criteria: Recovery to be 85-115% in ⅔ of aliquots at each dilution. For each of 11KT, 11OHA and 11OHT all replicates at each concentration were within 85-115% of the expected result allowing for a sample dilution of up to ¹⁄₁₀.

Example 10—Specificity

The specificity of the method was demonstrated by analyzing physiologically significant concentrations (1,000 ng/dL) of potentially interfering steroid compounds.

Acceptance Criteria: Response in the analyte transition to be less than the LLOQ.

For 11KT, the analytical response for all potentially interfering compounds (added a concentration of 1,000 ng/dL) was less than the LLOQ of 1.0 ng/dL 0.25 ng/dL).

For 11OHA, the analytical response for all potentially interfering compounds was less than the LLOQ of 3.0 ng/dL (≤0.23 ng/dL).

For 11OHT, the analytical response for all potentially interfering compounds was less than the LLOQ of 1.0 ng/dL. (≤0.25 ng/dL).

The potentially interfering compounds that were assessed are shown below.

| Potentially Interfering Compounds | |
| --- | --- |
| 17α-Hydroxypregnenolone | 17-α-Methyltestosterone |
| 5α-Androstane | 19-Nortestosterone |
| 4-Androsten-3,17-dione | 4-Pregnen-20α-ol-3-one |
| Androsterone | 4-Pregnen-20β-ol-3-one |
| 4-Pregnen-17,21-diol-3,11,20-trione | 21-Deoxycortisol |
| | 4-Androsten-3β,17β-diol |
| Hydrocortisone | 5α-Androstan-3β,17β-diol |
| Dexamethasone | 5α-Androstan-3β-ol |
| 5α-Androstan-17β-ol-3-one | 5β-Androstan-3α,17α-diol |
| trans-Androsterone | Aldosterone |
| β-Estradiol | Beclomethasone |
| Estriol | Beclomethasone dipropionate |
| Estrone | trans-Dehydroandrosterone |
| Prednisolone | Corticosterone |
| Prednisone | Deoxycorticosterone |
| Progesterone | 5β-Pregnan-3α,20α-diol |
| Testosterone | 5-Pregnen-3β-ol-20-one |
| 4-Pregnen-11α-ol-3,20-dione | Etiocholan-3α-ol-17-one |
| Reichstein's Substance S | 5α-Androstane-3α,17α-diol |
| 17α-Hydroxyprogesterone | Tetrahyrocortisol |
| | Tetrahydrocortisone |

Example 11—Short Term Stability in Human Serum and Stripped Serum and Three Months Stability A. Serum Short term stability in serum was determined by drawing 6 healthy volunteers and subjecting aliquots of their serum to various stability conditions including freezing at less than minus 55 degrees C. for 17 days, and room temperature (15 to 30 degrees C.) for 2 hours, 1 day, 3 days, 14 days; freezing at less than (<) minus 10 degrees C. for 14 days, maintained at 2 to 8 degrees C. (2 hours, 3 days or 14 days), or 6 freeze-thaw cycles. Serum stored at each stability condition was analyzed in triplicate and the results compared to the mean result of serum analyzed on the day of the draw.

Acceptance Criteria: Post stability concentration of analyte to be within 85-115% of mean baseline result in at least ⅔ of replicates from at least ⅔ of donors.

For 11KT, stability has been demonstrated for at least 17 days at <−55° C., 14 days at <−10° C., 14 days refrigerated at 2-8° C., 14 days at room temperature at 15-30° C., 6 freeze/thaw cycles, at least 1 day stored on whole blood at 2-8° C., and at least 2 hours stored on whole blood at 15-30° C.

11OHA stability has been demonstrated for at least 17 days at <−55° C., 14 days at <−10° C., 14 days refrigerated at 2-8° C., 14 days at room temperature at 15-30° C., 6 freeze/thaw cycles, at least 3 days stored on whole blood at 2-8° C., and at least 3 days stored on whole blood at 15-30° C.

11OHT stability has been demonstrated for at least 28 days at <−55° C., 14 days at <−10° C., 14 days refrigerated at 2-8° C., 14 days at room temperature at 15-30° C., 6 freeze/thaw cycles, at least 1 day stored on whole blood at 2-8° C., and at least 2 days stored on whole blood at 15-30° C.

B. Stripped Serum

Short term stability in stripped serum was determined by preparing 3 concentrations of each analyte in charcoal stripped serum and subjecting aliquots to various stability conditions. Stripped serum stored at each stability condition was analyzed in triplicate and the results compared to the mean baseline result analyzed on the day of preparation.

Acceptance Criteria: Post stability concentration of analyte to be within 85-115% of mean baseline result in at least ⅔ of replicates from at least ⅔ of donors. For each of 11KT, 11OHA and 11OHT, stability has been demonstrated for at least 17 days at <−55° C., 14 days at <−10° C., 14 days refrigerated at 2-8° C., 14 days at room temperature at 15-30° C., and for 6 freeze/thaw cycles.

C. Three Months Stability

Aliquots of serum from healthy volunteers used for short term stability were stored for three months at <−10° C. Each serum was analyzed in triplicate and the results compared to the mean result of serum analyzed on the day of the draw.

Acceptance Criteria: Post stability concentration of analyte to be within 85-115% of mean baseline result in at least ⅔ of replicates from at least ⅔ of donors. For each of 11KT, 11OHA and 11OHT, stability has been demonstrated for at least 3 months at <−10° C.

Example 12—Autosampler Stability

Autosampler stability was demonstrated by preparing an assay and analyzing it on the LC-MS/MS that day, leaving the processed assay in the autosampler at 10° C. for at least 48 hours, and then re-analyzing it.

Acceptance Criteria: Post stability concentration of analyte to be within 85-115% of mean baseline result in at least ⅔ of the samples tested. The autosampler stability experiment was for 84 hours with 10% acetonitrile in water as the storage buffer. 11KT met acceptance criteria with 65 of 68 (95.6%) post-stability results within 85-115% of the original and a mean recovery of 100.1%. 11OHA met acceptance criteria with 60 of 68 (88.2%) of post-stability results within 85-115% of the original result and a mean recovery of 105.1%. 11OHT met acceptance criteria with 47 of 68 (69.1%) of post-stability results within 85-115% of the original result and a mean recovery of 107.1%.

Example 13—Benchtop Stability

Benchtop stability was demonstrated by preparing 2 assays and analyzing one on the LC-MS/MS that day, leaving the other assay on the benchtop at 15-30° C. for at least 48 hours, and then analyzing it. Original tests employed methanol:water as the reconstitution buffer, but it was found that 11KT and 11OHA are more stable in acetonitrile:water.

Acceptance Criteria: Post stability concentration of analyte to be within 85-115% of mean baseline result in at least ⅔ of the samples tested.

11KT met acceptance criteria with 64 of 68 (94.1%) post-stability results within 85-115% of the original and a mean recovery of 101.3%.

11OHT met acceptance criteria with 52 of 68 (76.5%) post-stability results within 85-115% of the original and a mean recovery of 106.6%.

11OHA also met acceptance criteria with 60 of 68 (88.2%) of post-stability results within 85-115% of the original result and a mean recovery of 100.9%.

Example 14—Standard Curve Accuracy and Imprecision

Standard accuracy and imprecision was demonstrated by compiling the back-calculated concentrations of the standards in 6 assays. Eight standard points were included in each run to define the calibration curve. Standard curves were adjusted by excluding no more than 25% of data points which exceeded ±15% (±20% at the LLOQ) of the target concentration.

Acceptance Criteria: A minimum of 6 acceptable points per standard curve with back-calculated accuracy within ±15% (±20% at the LLOQ) of the target concentration are required for a valid standard curve. Inter-assay accuracy to be 85% to 115% (80% to 120% at the LLOQ), and % CV to be <15% (<20% at the LLOQ).

For 11KT, the inter-assay accuracy over six assays at the LLOQ was 102.9% and ranged from 97.4% to 101.8% at the other concentrations. Inter-assay imprecision was 11.5% CV at the LLOQ and ranged from 2.9 to 4.8% CV at the other concentrations. All 6 standard curves meet acceptance requirements.

For 11OHA, the inter-assay accuracy over six assays at the low standard was 102.9% and ranged from 97.6% to 103.1% at the other concentrations. Inter-assay imprecision was 17.2% CV at the LLOQ and ranged from 2.8 to 8.1% CV at the other concentrations. All 6 standard curves meet acceptance requirements.

For 11OHT, the inter-assay accuracy over the six assays at the low standard was 100.6% and ranged from 96.5% to 102.5% at the other concentrations. Inter-assay imprecision was 19.7% CV at the LLOQ and ranged from 2.4 to 7.4% CV at the other concentrations. All 6 standard curves meet acceptance requirements.

Example 15—Reference Interval

Reference intervals for 11KT, 11OHA, and 11OHT were determined by analyzing a minimum of 120 adult female and 120 adult male serum samples with thyroid stimulating hormone results in the reference interval of that assay. Validation Batches contained patient samples for male and female reference interval determination but those samples were not screened to determine if they were acceptable reference interval samples. Additional patient serum samples were screened for testosterone and androstenedione. Only samples with results within the reference interval for testosterone and androstenedione were used for 11-oxy steroids reference interval testing.

One hundred twenty three adult male samples and 137 adult female samples were tested for 11-oxy steroids reference interval (FIG. 5). The adult female reference interval for 11KT is 5.0 to 60.6 ng/dL. The adult male reference interval for 11KT is 9.5 to 70.8 ng/dL. The adult female reference interval for 11OHA is 19.2 to 333 ng/dL. The adult male reference interval for 11OHA is 36.4 to 313 ng/dL. The adult female reference interval for 11OHT is <39.8 ng/dL. The adult male reference interval for 11OHT is 5.2 to 43.4 ng/dL.

Example 16—Embodiments

A.1. A method for determining the presence or amount of at least one 11-oxo androgen in a sample by tandem mass spectrometry, comprising:
 (a) obtaining a sample from a subject;
 (b) optionally adding a stable isotope labeled 11-oxo androgen to the sample as an internal standard;
 (c) performing liquid chromatography to purify the sample; and
 (d) measuring the 11-oxo androgen by tandem mass spectrometry.

A.2. The method of any one of the previous and/or subsequent embodiments, wherein the sample is a biological sample.

A.3. The method of any one of the previous and/or subsequent embodiments, wherein the biological sample comprises one of blood, plasma, serum, urine, saliva, tear, cerebrospinal fluid, organ, hair, muscle, or other tissue sample.

A.4. The method of any one of the previous and/or subsequent embodiments, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample.

A.5. The method of any one of the previous and/or subsequent embodiments, wherein the liquid chromatography comprises high performance liquid chromatography (HPLC).

A.6. The method of any one of the previous and/or subsequent embodiments, wherein the liquid chromatography comprises high turbulence liquid chromatography (HTLC).

A.7. The method of any one of the previous and/or subsequent embodiments, wherein the 11-oxo androgen may comprise at least one of 11-hydroxyandrostendione (11OHA), 11-hydroxytestosterone (11OHT) or 11-ketotestosterone (11KT).

A.8. The method of any one of the previous and/or subsequent embodiments, further comprising at least one purification step prior to mass spectrometry.

A.9. The method of any one of the previous and/or subsequent embodiments, wherein the purification step is a liquid-liquid extraction (LLE).

A.10. The method of any one of the previous and/or subsequent embodiments, wherein the tandem mass spectrometry uses positive ion atmospheric pressure chemical ionization (APCI) mode.

A.11. The method of any one of the previous and/or subsequent embodiments, further comprising determining a back-calculated amount of the 11-oxo androgen in the sample by spiking known amounts of each purified 11-oxo androgen into charcoal stripped serum to generate calibration curves.

A.12. The method of any one of the previous and/or subsequent embodiments, further comprising analyzing duplicate sets of charcoal stripped calibrators in each batch.

A.13. The method of any one of the previous and/or subsequent embodiments, wherein known amounts of the at least one 11-oxo androgen are added to to charcoal stripped calibrators generate a final concentration of purified analyte of interest that is within the range of about 3.0 to 1,000 ng/dL.

A.14. The method of any one of the previous and/or subsequent embodiments, wherein the tandem mass spectrometry is performed in a manner so as to measure multiple precursor-fragment transitions for the at least one 11-oxo-androgen.

A.15. The method of any one of the previous and/or subsequent embodiments, wherein the tandem mass spectrometry comprises selecting one or more fragment ions for quantitation of the at least one 11-oxo androgen and selecting one or more additional qualifier fragment ions as a qualitative standard.

A.16. The method of any one of the previous and/or subsequent embodiments, wherein the at least one 11-oxo-androgen is 11-hydroxyandrostendione (11OHA).

A.17. The method of any one of the previous and/or subsequent embodiments, wherein for 11OHA, the precursor ion has a mass/charge ratio (m/z) of about 303.401; the one or more fragment ions for quantitation comprise a fragment ion with a m/z of about 121.100; and the one or more additional qualifier fragment ions comprise a fragment ion with a m/z of about 105.100 and/or about 97.100.

A.18. The method of any one of the previous and/or subsequent embodiments, further comprising adding $^2H_4$-11β-hydroxyandrostenedione as an internal standard.

A.19. The method of any one of the previous and/or subsequent embodiments, wherein for $^2H_4$-11β-hydroxyandrostenedione, the tandem mass spectrometry generates a precursor ion for the internal standard with a mass to charge ratio (m/z) of about 308.400 and a fragment ion with a m/z of about 122.200.

A.20. The method of any one of the previous and/or subsequent embodiments, wherein the at least one 11-oxo-androgen is 11-ketotestosterone (11KT).

A.21. The method of any one of the previous and/or subsequent embodiments, wherein for 11KT, the precursor ion has a mass/charge ratio (m/z) of about 303.400; the one or more fragment ions for quantitation comprise a fragment ion with a m/z of about 121.200; and the one or more additional qualifier fragment ions comprise a fragment ion with a m/z of about 105.200 and/or about 91.200.

A.22. The method of any one of the previous and/or subsequent embodiments, further comprising adding $^2H_3$-11β-ketotestosterone as an internal standard.

A.23. The method of any one of the previous and/or subsequent embodiments, wherein for $^2H_3$-11β-ketotestosterone, the tandem mass spectrometry generates a precursor ion for the internal standard with a mass/charge ratio (m/z) of about 306.400 and a fragment ion with a m/z of about 121.200.

A.24. The method of any one of the previous and/or subsequent embodiments, wherein the at least one 11-oxo-androgen is 11-hydroxytestosterone (11OHT).

A.25. The method of any one of the previous and/or subsequent embodiments, wherein for 11OHT, the precursor ion has a mass/charge ratio (m/z) of about 305.400; the one or more fragment ions for quantitation comprise a fragment ion with a m/z of about 121.100; and the one or more additional qualifier fragment ions comprise a fragment ion with a m/z of about 105.000 and 97.000.

A.26. The method of any one of the previous and/or subsequent embodiments, further comprising adding $^2H_4$-11β-hydroxytestosterone as an internal standard.

A.27. The method of any one of the previous and/or subsequent embodiments, wherein for $^2H_4$-11β-hydroxytestosterone, the mass spectrometry generates a precursor ion for the internal standard with a mass/charge ratio (m/z) of about 309.200 m/z and a fragment ion with an m/z of about 121.100.

A.28. The method of any one of the previous and/or subsequent embodiments, comprising detection of 11OHA over a range of from 3.0 ng/dL to 1,000 ng/dL, and/or detection of 11OHT over a range of from 1.0 ng/dL to 1,000 ng/dL, and/or detection of 11KT over a range of from 1.0 ng/dL to 1,000 ng/dL.

B.1. A system for determining the presence or amount of at least one biomarker of interest in a test sample, the system comprising:
 a station for providing a test sample suspected of containing one or more 11-oxo androgens;
 a station for partially purifying the one or more 11-oxo androgens from other components in the sample;
 a station for chromatographically separating one or more 11-oxo androgen from other components in the sample; and
 a station for analyzing the chromatographically separated one or more 11-oxo androgens by mass spectrometry to determine the presence or amount of the one or more 11-oxo androgens in the test sample.

B.2. The system of any one of the previous and/or subsequent embodiments, further comprising a station to add at least one internal standard for the at least one biomarker of interest.

B.3. The system of any one of the previous and/or subsequent embodiments, wherein the station for partially purifying one or more 11-oxo androgens comprises a station to perform at least one of liquid-liquid extraction, solid phase extraction, or protein precipitation.

B.4. The system of any one of the previous and/or subsequent embodiments, wherein the station for chromatographically separating one or more 11-oxo androgens comprises a station to perform high performance liquid chromatography (HPLC) or high turbulence liquid chromatography (HTLC).

B.5. The system of any one of the previous and/or subsequent embodiments, wherein the station for analyzing chromatographically separated one or more 11-oxo androgens comprises a tandem mass spectrometer.

B.6. The system of any one of the previous and/or subsequent embodiments, wherein at least one of the stations is controlled by a computer.

B.7. The system of any one of the previous and/or subsequent embodiments, wherein the sample is a biological sample.

B.8. The system of any one of the previous and/or subsequent embodiments, wherein the biological sample comprises one of blood, plasma, serum, urine, saliva, tear, cerebrospinal fluid, organ, hair, muscle, or other tissue sample.

B.9. The system of any one of the previous and/or subsequent embodiments, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample.

B.10. The system of any one of the previous and/or subsequent embodiments, wherein the 11-oxo androgen may comprise at least one of 11-hydroxyandrostendione (11OHA), 11-hydroxytestosterone (11OHT) or 11-ketotestosterone (11KT).

B.11. The system of any one of the previous and/or subsequent embodiments, wherein the purification step is a liquid-liquid extraction (LLE).

B.12. The system of any one of the previous and/or subsequent embodiments, wherein the tandem mass spectrometry uses positive ion atmospheric pressure chemical ionization (APCI) mode.

B.13. The system of any one of the previous and/or subsequent embodiments, further comprising a station for determining a back-calculated amount of the 11-oxo androgen in the sample by spiking known amounts of each purified 11-oxo androgen into charcoal stripped serum to generate calibration curves.

B.14. The system of any one of the previous and/or subsequent embodiments, wherein known amounts of the at least one 11-oxo androgen are added to to charcoal stripped calibrators generate a final concentration of purified analyte of interest that is within the range of about 3.0 to 1,000 ng/dL.

B.15. The system of any one of the previous and/or subsequent embodiments, wherein the tandem mass spectrometry is performed in a manner so as to measure multiple precursor-fragment transitions for the at least one 11-oxo-androgen.

B.16. The system of any one of the previous and/or subsequent embodiments, wherein the tandem mass spectrometry comprises selecting one or more fragment ions for quantitation of the at least one 11-oxo androgen and selecting one or more additional qualifier fragment ions as a qualitative standard.

B.17. The system of any one of the previous and/or subsequent embodiments, wherein the at least one 11-oxo-androgen is 11-hydroxyandrostendione (11OHA).

B.18. The system of any one of the previous and/or subsequent embodiments, wherein for 11OHA, the precursor ion has a mass/charge ratio (m/z) of about 303.401; the one or more fragment ions for quantitation comprise a fragment ion with a m/z of about 121.100; and the one or more additional qualifier fragment ions comprise a fragment ion with a m/z of about 105.100 and/or about 97.100.

B.19. The system of any one of the previous and/or subsequent embodiments, further comprising adding $^2H_4$-11β-hydroxyandrostenedione as an internal standard.

B.20. The system of any one of the previous and/or subsequent embodiments, wherein for $^2H_4$-11β-hydroxyandrostenedione, the tandem mass spectrometry generates a precursor ion for the internal standard with a mass to charge ratio (m/z) of about 308.400 and a fragment ion with a m/z of about 122.200.

B.21. The system of any one of the previous and/or subsequent embodiments, wherein the at least one 11-oxo-androgen is 11-ketotestosterone (11KT).

B.22. The system of any one of the previous and/or subsequent embodiments, wherein for 11KT, the precursor ion has a mass/charge ratio (m/z) of about 303.400; the one or more fragment ions for quantitation comprise a fragment ion with a m/z of about 121.200; and the one or more additional qualifier fragment ions comprise a fragment ion with a m/z of about 105.200 and/or about 91.200.

B.23. The system of any one of the previous and/or subsequent embodiments, further comprising adding $^2H_3$-11β-ketotestosterone as an internal standard.

B.24. The system of any one of the previous and/or subsequent embodiments, wherein for $^2H_3$-11β-ketotestosterone, the tandem mass spectrometry generates a precursor ion for the internal standard with a mass/charge ratio (m/z) of about 306.400 and a fragment ion with a m/z of about 121.200.

B.25. The system of any one of the previous and/or subsequent embodiments, wherein the at least one 11-oxo-androgen is 11-hydroxytestosterone (11OHT).

B.26. The system of any one of the previous and/or subsequent embodiments, wherein for 11OHT, the precursor ion has a mass/charge ratio (m/z) of about 305.400; the one or more fragment ions for quantitation comprise a fragment ion with a m/z of about 121.100; and the one or more additional qualifier fragment ions comprise a fragment ion with a m/z of about 105.000 and 97.000.

B.27. The system of any one of the previous and/or subsequent embodiments, further comprising adding $^2H_4$-11β-hydroxytestosterone as an internal standard.

B.28. The system of any one of the previous and/or subsequent embodiments, wherein for $^2H_4$-11β-hydroxytestosterone, the mass spectrometry generates a precursor ion for the internal standard with a mass/charge ratio (m/z) of about 309.200 m/z and a fragment ion with an m/z of about 121.100.

B.29. The system of any one of the previous and/or subsequent embodiments, comprising detection of 11OHA over a range of from 3.0 ng/dL to 1,000 ng/dL, and/or detection of 11OHT over a range of from 1.0 ng/dL to 1,000 ng/dL, and/or detection of 11KT over a range of from 1.0 ng/dL to 1,000 ng/dL.

C.1. A computer-program product tangibly embodied in a non-transitory machine-readable storage medium, including instructions configured to cause one or more data processors to perform actions to measure the presence or amount of at least one 11-oxo androgen in a sample comprising at least one of the following steps:
  (a) obtaining a sample from a subject;
  (b) optionally adding a stable isotope-labeled 11-oxo androgen to the sample as an internal standard;
  (c) performing liquid chromatography; and
  (d) measuring the 11-oxo androgen by tandem mass spectrometry.

C.2. The computer-program product of any one of the previous and/or subsequent embodiments, wherein the sample is a biological sample.

C.3. The computer-program product of any one of the previous and/or subsequent embodiments, wherein the biological sample comprises one of blood, plasma, serum, urine, saliva, tear, cerebrospinal fluid, organ, hair, muscle, or other tissue sample.

C.4. The computer-program product of any one of the previous and/or subsequent embodiments, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample.

C.5. The computer-program product of any one of the previous and/or subsequent embodiments, wherein the liquid chromatography comprises high performance liquid chromatography (HPLC).

C.6. The computer-program product of any one of the previous and/or subsequent embodiments, wherein the liquid chromatography comprises high turbulence liquid chromatography (HTLC).

C.7. The computer-program product of any one of the previous and/or subsequent embodiments, wherein the 11-oxo androgen may comprise at least one of 11-hydroxyandrostendione (11OHA), 11-hydroxytestosterone (11OHT) or 11-ketotestosterone (11KT).

C.8. The computer-program product of any one of the previous and/or subsequent embodiments, further comprising instructions for at least one purification step prior to mass spectrometry.

C.9. The computer-program product of any one of the previous and/or subsequent embodiments, wherein the purification step is a liquid-liquid extraction (LLE).

C.10. The computer-program product method of any one of the previous and/or subsequent embodiments, wherein the tandem mass spectrometry uses positive ion atmospheric pressure chemical ionization (APCI) mode.

C.11. The computer-program product of any one of the previous and/or subsequent embodiments, further comprising instructions for determining a back-calculated amount of the 11-oxo androgen in the sample by spiking known amounts of each purified 11-oxo androgen into charcoal stripped serum to generate calibration curves.

C.12. The computer-program product of any one of the previous and/or subsequent embodiments, further comprising instructions for analyzing duplicate sets of charcoal stripped calibrators in each batch.

C.13. The computer-program product of any one of the previous and/or subsequent embodiments, further comprising instructions for adding known amounts of the at least one 11-oxo androgen to charcoal stripped calibrators generate a final concentration of purified analyte of interest that is within the range of about 3.0 to 1,000 ng/dL.

C.14. The computer-program product of any one of the previous and/or subsequent embodiments, wherein the tandem mass spectrometry is performed in a manner so as to measure multiple precursor-fragment transitions for the at least one 11-oxo-androgen.

C.15. The computer-program product of any one of the previous and/or subsequent embodiments, wherein the tandem mass spectrometry comprises selecting one or more fragment ions for quantitation of the at least one 11-oxo androgen and selecting one or more additional qualifier fragment ions as a qualitative standard.

C.16. The computer-program product of any one of the previous and/or subsequent embodiments, wherein the at least one 11-oxo-androgen is 11-hydroxyandrostenedione (11OHA).

C.17. The computer-program product of any one of the previous and/or subsequent embodiments, wherein for 11OHA, the precursor ion has a mass/charge ratio (m/z) of about 303.401; the one or more fragment ions for quantitation comprise a fragment ion with a m/z of about 121.100; and the one or more additional qualifier fragment ions comprise a fragment ion with a m/z of about 105.100 and/or about 97.100.

C.18. The computer-program product of any one of the previous and/or subsequent embodiments, further comprising instructions for adding $^2H_4$-11β-hydroxyandrostenedione as an internal standard.

C.19. The computer-program product of any one of the previous and/or subsequent embodiments, wherein for $^2H_4$-11β-hydroxyandrostenedione, the tandem mass spectrometry generates a precursor ion for the internal standard with a mass to charge ratio (m/z) of about 308.400 and a fragment ion with a m/z of about 122.200.

C.20. The computer-program product of any one of the previous and/or subsequent embodiments, wherein the at least one 11-oxo-androgen is 11-ketotestosterone (11KT).

C.21. The computer-program product of any one of the previous and/or subsequent embodiments, wherein for 11KT, the precursor ion has a mass/charge ratio (m/z) of about 303.400; the one or more fragment ions for quantitation comprise a fragment ion with a m/z of about 121.200; and the one or more additional qualifier fragment ions comprise a fragment ion with a m/z of about 105.200 and/or about 91.200.

C.22. The computer-program product of any one of the previous and/or subsequent embodiments, further comprising instructions for adding $^2H_3$-11β-ketotestosterone as an internal standard.

C.23. The computer-program product of any one of the previous and/or subsequent embodiments, wherein for $^2H_3$-11β-ketotestosterone, the tandem mass spectrometry generates a precursor ion for the internal standard with a mass/charge ratio (m/z) of about 306.400 and a fragment ion with a m/z of about 121.200.

C.24. The computer-program product of any one of the previous and/or subsequent embodiments, wherein the at least one 11-oxo-androgen is 11-hydroxytestosterone (11OHT).

C.25. The computer-program product of any one of the previous and/or subsequent embodiments, wherein for 11OHT, the precursor ion has a mass/charge ratio (m/z) of about 305.400; the one or more fragment ions for quantitation comprise a fragment ion with a m/z of about 121.100; and the one or more additional qualifier fragment ions comprise a fragment ion with a m/z of about 105.000 and 97.000.

C.26. The computer-program product of any one of the previous and/or subsequent embodiments, further comprising instructions for adding $^2H_4$-11β-hydroxytestosterone as an internal standard.

C.27. The computer-program product of any one of the previous and/or subsequent embodiments, wherein for $^2H_4$-11β-hydroxytestosterone, the mass spectrometry generates a precursor ion for the internal standard with a mass/charge ratio (m/z) of about 309.200 m/z and a fragment ion with an m/z of about 121.100.

C.28. The computer-program product of any one of the previous and/or subsequent embodiments, comprising detection of 11OHA over a range of from 3.0 ng/dL to 1,000 ng/dL, and/or detection of 11OHT over a range of from 1.0 ng/dL to 1,000 ng/dL, and/or detection of 11KT over a range of from 1.0 ng/dL to 1,000 ng/dL.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

That which is claimed:

1. A method for determining the presence or amount of at least one 11-oxo androgen in a sample by tandem mass spectrometry, comprising:
    (a) obtaining a sample from a subject;
    (b) optionally adding a stable isotope labeled 11-oxo androgen to the sample as an internal standard;
    (c) performing liquid chromatography to purify the sample; and
    (d) measuring the 11-oxo androgen by tandem mass spectrometry, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample, and wherein the tandem mass spectrometry further comprises selecting one or more fragment ions for quantitation of the at least one 11-oxo androgen and selecting one or more additional qualifier fragment ions as a qualitative standard.

2. The method of claim 1, wherein the sample is a biological sample.

3. The method of claim 2, wherein the biological sample comprises one of blood, plasma, serum, urine, saliva, tear, cerebrospinal fluid, organ, hair, muscle, or other tissue sample.

4. The method of claim 1, wherein the liquid chromatography comprises high performance liquid chromatography (HPLC).

5. The method of claim 1, wherein the at least one 11-oxo-androgen is 11-hydroxyandrostenedione (11OHA).

6. The method of claim 5, wherein the precursor ion has a mass/charge ratio (m/z) of about 303.401; the one or more fragment ions for quantitation comprise a fragment ion with a m/z of about 121.100; and the one or more additional qualifier fragment ions comprise a fragment ion with a m/z of about 105.100 and/or about 97.100.

7. The method of claim 5, further comprising adding $^2H_4$-11β-hydroxyandrostenedione as an internal standard.

8. The method of claim 1, wherein the at least one 11-oxo-androgen is 11-hydroxytestosterone (11OHT).

9. The method of claim 8, wherein the precursor ion has a mass/charge ratio (m/z) of about 305.400; the one or more fragment ions for quantitation comprise a fragment ion with a m/z of about 121.100; and the one or more additional qualifier fragment ions comprise a fragment ion with a m/z of about 105.000 and 97.000.

10. The method of claim 8, further comprising adding $^2H_4$-11β-hydroxytestosterone as an internal standard.

11. The method of claim 1, comprising detection of 11OHA over a range of from 3.0 ng/dL to 1,000 ng/dL, and/or detection of 11OHT over a range of from 1.0 ng/dL to 1,000 ng/dL, and/or detection of 11KT over a range of from 1.0 ng/dL to 1,000 ng/dL.

12. The method of claim 1, wherein the at least one 11-oxo-androgen is 11-ketotestosterone (11KT).

13. The method of claim 12, wherein the precursor ion has a mass/charge ratio (m/z) of about 303.400; the one or more fragment ions for quantitation comprise a fragment ion with a m/z of about 121.200; and the one or more additional qualifier fragment ions comprise a fragment ion with a m/z of about 105.200 and/or about 91.200.

14. The method of claim 12, further comprising adding $^2H_3$-11β-ketotestosterone as an internal standard.

15. The method of claim 1, wherein the 11-oxo androgen may comprise at least one of 11-hydroxyandrostendione (11OHA), 11-hydroxytestosterone (11OHT) or 11-ketotestosterone (11KT).

16. The method of claim 1, further comprising determining a back-calculated amount of the 11-oxo androgen in the sample by spiking known amounts of each purified 11-oxo androgen into charcoal stripped serum to generate calibration curves.

17. A system for determining the presence or amount of at least one biomarker of interest in a test sample, the system comprising:
- a station for providing a test sample suspected of containing one or more 11-oxo androgens;
- a station for partially purifying the one or more 11-oxo androgens from other components in the sample;
- a station for chromatographically separating one or more 11-oxo androgen from other components in the sample; and
- a station for analyzing the chromatographically separated one or more 11-oxo androgens by mass spectrometry to determine the presence or amount of the one or more 11-oxo androgens in the test sample, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample, and wherein the tandem mass spectrometry comprises selecting one or more fragment ions for quantitation of the at least one 11-oxo androgen and selecting one or more additional qualifier fragment ions as a qualitative standard.

18. A computer-program product tangibly embodied in a non-transitory machine-readable storage medium, including instructions configured to cause one or more computers to perform actions to measure the presence or amount of at least one 11-oxo androgen in a sample comprising at least one of the following steps:
- (a) obtaining a sample from a subject;
- (b) optionally adding a stable isotope-labeled 11-oxo androgen to the sample as an internal standard;
- (c) performing liquid chromatography; and
- (d) measuring the 11-oxo androgen by tandem mass spectrometry, wherein the tandem mass spectrometry comprises the steps of: (i) generating a precursor ion of the 11-oxo androgen; (ii) generating one or more fragment ions of the precursor ion; and (ii) detecting the presence or amount of the precursor ion generated in step (i) and/or the at least one or more fragment ions generated in step (ii), or both, and relating the detected ions to the presence or amount of the 11-oxo androgen in the sample, and wherein the tandem mass spectrometry comprises selecting one or more fragment ions for quantitation of the at least one 11-oxo androgen and selecting one or more additional qualifier fragment ions as a qualitative standard.

* * * * *